(12) United States Patent
Iannotti et al.

(10) Patent No.: US 8,926,627 B2
(45) Date of Patent: Jan. 6, 2015

(54) APPARATUS AND METHOD FOR TRANSFERRING PREDETERMINED SPATIAL POSITIONING INFORMATION TO AN ADJUSTABLE TOOL

(75) Inventors: Joseph P. Iannotti, Strongsville, OH (US); Wael K. Barsoum, Bay Village, OH (US); Jason A. Bryan, Avon Lake, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 221 days.

(21) Appl. No.: 13/606,160

(22) Filed: Sep. 7, 2012

(65) Prior Publication Data

US 2013/0237991 A1   Sep. 12, 2013

Related U.S. Application Data

(60) Provisional application No. 61/534,142, filed on Sep. 13, 2011.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61F 2/46* | (2006.01) | |
| *A61F 2/30* | (2006.01) | |
| *A61F 2/40* | (2006.01) | |
| *A61B 17/17* | (2006.01) | |

(52) U.S. Cl.
CPC ........... *A61F 2/4657* (2013.01); *A61F 2/30724* (2013.01); *A61F 2/4603* (2013.01); *A61F 2/30942* (2013.01); *A61F 2/40* (2013.01); *A61F 2/4612* (2013.01); *A61F 2002/30726* (2013.01); *A61F 2002/4668* (2013.01); *A61F 2002/4687* (2013.01); *A61B 2017/1778* (2013.01)
USPC .......................................... 606/102; 606/86 R

(58) Field of Classification Search
CPC .................... A61B 17/1767; A61B 17/1764
USPC .......................................... 606/86 R, 87, 102
See application file for complete search history.

(56) References Cited

U.S. PATENT DOCUMENTS

| | | | |
|---|---|---|---|
| 2,666,430 A | 1/1954 | Gispert | |
| 2,697,433 A | 12/1954 | Zehnder | |
| 5,190,547 A * | 3/1993 | Barber et al. | 606/79 |
| 2008/0132903 A1 | 6/2008 | Yoon | |
| 2010/0234850 A1 | 9/2010 | Dees, Jr. et al. | |

* cited by examiner

*Primary Examiner* — Andrew Yang
(74) *Attorney, Agent, or Firm* — Tarolli, Sundheim, Covell & Tummino LLP

(57) ABSTRACT

An apparatus transfers predetermined spatial positioning information to an adjustable tool. Means are provided for temporarily holding at least a carrier portion of the adjustable tool stationary relative to a manipulable reference surface. Means are provided for imparting predetermined spatial positioning information to the reference surface in a first degree of freedom. Means are provided for imparting predetermined spatial positioning information to the reference surface in a second degree of freedom. The predetermined spatial positioning information is imparted to the reference surface in the first and second degrees of freedom to generate a pre-set reference surface. At least a portion of the adjustable tool is held stationary relative to the pre-set reference surface. At least a functional portion of the adjustable tool is manipulated into a predetermined setting position relative to the reference surface. The predetermined setting position reflects a position of the pre-set reference surface.

21 Claims, 21 Drawing Sheets

APPARATUS AND METHOD FOR TRANSFERRING PREDETERMINED SPATIAL POSITIONING INFORMATION TO AN ADJUSTABLE TOOL

RELATED APPLICATION

This application claims priority from U.S. Provisional Application No. 61/534,142, filed 13 Sep. 2011, the subject matter of which is incorporated herein by reference in its entirety.

TECHNICAL FIELD

The present invention relates to an apparatus and method for transferring predetermined spatial positioning information to an adjustable tool and, more particularly, to a method of setting an adjustable tool for use in a particular surgical environment.

BACKGROUND OF THE INVENTION

In the installation of a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault.

Because the shoulder prosthesis is normally provided to correct a congenital or acquired defect of the native shoulder joint, the glenoid vault or surface often exhibits a pathologic, nonstandard anatomic configuration. A surgeon must compensate for such pathologic glenoid vault anatomy when implanting the glenoid component in striving to achieve a solid anchoring of the glenoid component into the glenoid vault. Detailed preoperative planning, using two- or three-dimensional internal images of the shoulder joint, often assists the surgeon in compensating for the patient's anatomical limitations. During the surgery, one or more elongated pins may be inserted into the surface of the patient's bone, at a predetermined trajectory and location, to act as a passive landmark or active guiding structure in carrying out the pre-operatively planned implantation. These "guide pins" may remain as a portion of the implanted prosthetic joint or may be removed before the surgery is concluded. This type of pin-guided installation may be used with any joint replacement procedure—indeed, in any type of surgical procedure in which a surgeon-placed fixed landmark is desirable. For example, a hip replacement procedure may use a guide pin to facilitate installation of an acetabular prosthetic component into a pelvis in a similar manner to that described above for a shoulder replacement component. As another example, a guide pin could be placed in either a bony or "soft" patient tissue to serve as a substantially fixed landmark for any surgical reason and in any desirable patient tissue.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. Again, a guide pin may be temporarily or permanently placed into the exposed bone surface to help orient the surgeon and thereby enhance the accuracy and efficiency of the surgical procedure.

A carefully placed guide pin, regardless of the reason provided, will reduce the need for intraoperative imaging in most surgical procedures and should result in decreased operative time and increased positional accuracy, all of which are desirable in striving toward a positive patient outcome. Accordingly, a surgeon may be provided with an adjustable tool to dictate at least one of the insertion location and the insertion trajectory for the inserted guide pin, as desired by the surgeon and/or as predetermined through pre-operative or intraoperative planning. A suitable adjustable tool is disclosed in co-pending U.S. patent application Ser. No. 12/854,362, filed 11 Aug. 2010 and titled "Method and Apparatus for Insertion of an Elongate Pin into a Surface", which is incorporated herein by reference in its entirety and will be referenced as an example of an adjustable tool throughout this description. It will often be desirable for the adjustable tool to be "set" with the insertion location and/or insertion trajectory before or during the surgery, to minimize the time needed for placement of the pin.

SUMMARY OF THE INVENTION

In an embodiment of the present invention, an apparatus for transferring predetermined spatial positioning information to an adjustable tool is described. A manipulable reference surface is provided. Means are provided for temporarily holding at least a carrier portion of the adjustable tool stationary relative to the reference surface. Means are provided for imparting predetermined spatial positioning information to the reference surface in a first degree of freedom. Means are provided for imparting predetermined spatial positioning information to the reference surface in a second degree of freedom. The predetermined spatial positioning information is imparted to the reference surface in the first and second degrees of freedom to generate a pre-set reference surface. At least the carrier portion of the adjustable tool is then held stationary relative to the pre-set reference surface. Then, at least a functional portion of the adjustable tool is manipulated into a predetermined setting position relative to the reference surface. The predetermined setting position is reflective of a position of the pre-set reference surface.

In an embodiment of the present invention, a method of setting an adjustable tool for use in a particular surgical environment is described. A manipulable reference surface is provided. At least a carrier portion of the adjustable tool is temporarily held stationary relative to the reference surface. Predetermined spatial positioning information is imparted to the reference surface in a first degree of freedom. Predetermined spatial positioning information is imparted to the reference surface in a second degree of freedom. A pre-set reference surface embodying the predetermined spatial positioning information is generated. At least a functional portion of the adjustable tool is manipulated into a predetermined setting position reflective of the predetermined spatial positioning information embodied in the pre-set reference surface.

In an embodiment of the present invention, an apparatus for transferring predetermined spatial positioning information to an adjustable tool is described. An elongate column extends longitudinally upward from a base. A tool grasper is attached to the elongate column and is configured to temporarily hold at least a carrier portion of the adjustable tool stationary in relation to the base. A patient-specific spacing block is supported by the base. The spacing block includes a reference surface embodying predetermined spatial positioning information to be transferred to a functional portion of the adjustable tool.

In an embodiment of the present invention, an apparatus for transferring predetermined spatial positioning information to an adjustable tool is described. A manipulable reference surface is connected to a base. A tool grasper temporarily holds at least a carrier portion of the adjustable tool stationary relative to the reference surface. At least one adjustable orientation support imparts predetermined spatial positioning information to the reference surface in at least one degree of freedom. At least one other adjustable orientation support imparts predetermined spatial positioning information to the tool grasper in at least one degree of freedom. The predetermined spatial positioning information is imparted to at least one of the reference surface and the tool grasper to generate a pre-set reference surface in relation to the tool grasper. At least the carrier portion of the adjustable tool is then held stationary by the tool grasper relative to the preset reference surface. Then, at least a functional portion of the adjustable tool is manipulated into a predetermined setting position relative to the pre-set reference surface in relation to the tool grasper. The predetermined setting position is reflective of a position of the pre-set reference surface in relation to the tool grasper.

BRIEF DESCRIPTION OF THE DRAWINGS

For a better understanding of the invention, reference may be made to the accompanying drawings, in which.

DESCRIPTION OF EMBODIMENTS

Figure 1:
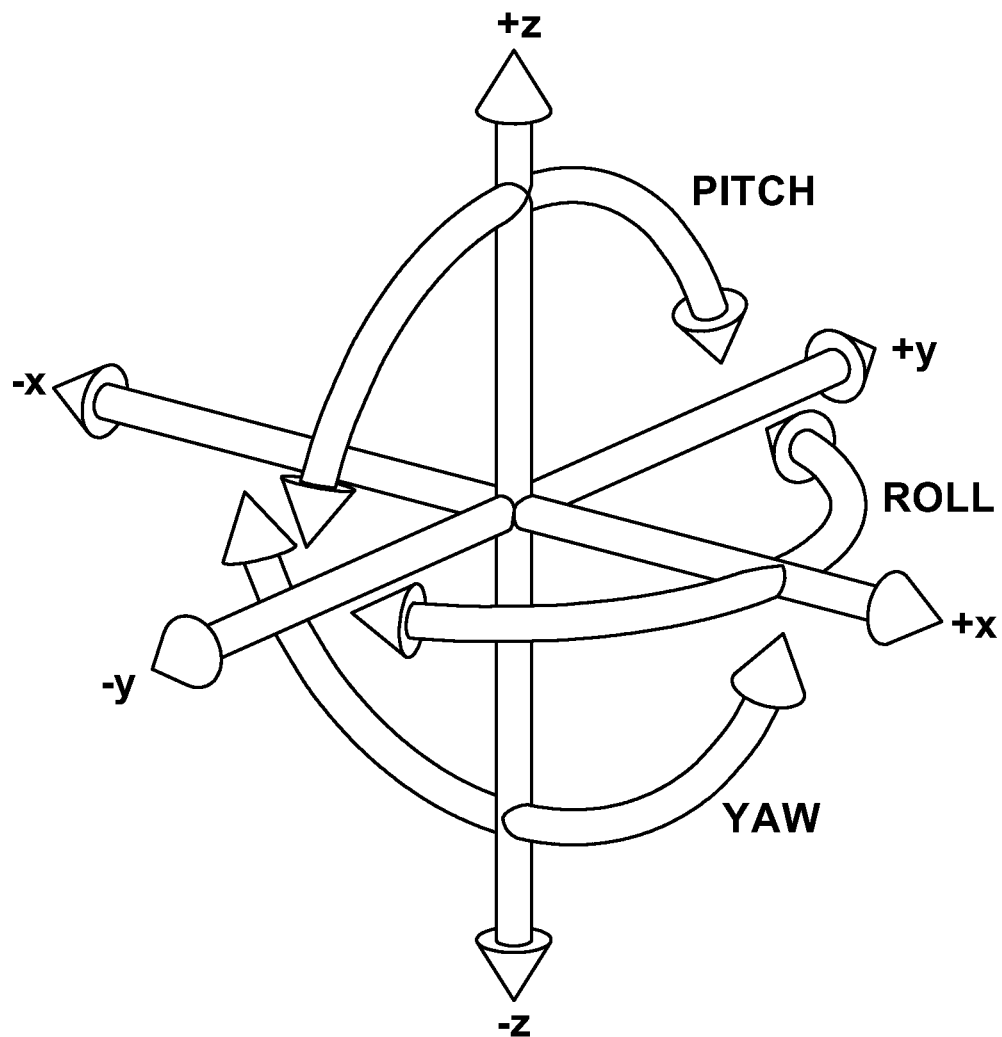
FIG. 1 is a perspective view of a coordinate system.

In accordance with the present invention, FIG. 1 depicts a coordinate system, showing six degrees of freedom (DOF) in which an unconstrained structure can move in space. The depicted DOF relate to the X-axis, Y-axis, Z-axis, pitch, yaw, and roll. The coordinate system of FIG. 1 will be referenced throughout this description. It should be noted that a partial coordinate system will be included in several later Figures, with the labeling convention that the "X", "Y", or "Z" label is shown on the positive end of the respective axis.

Figure 2:
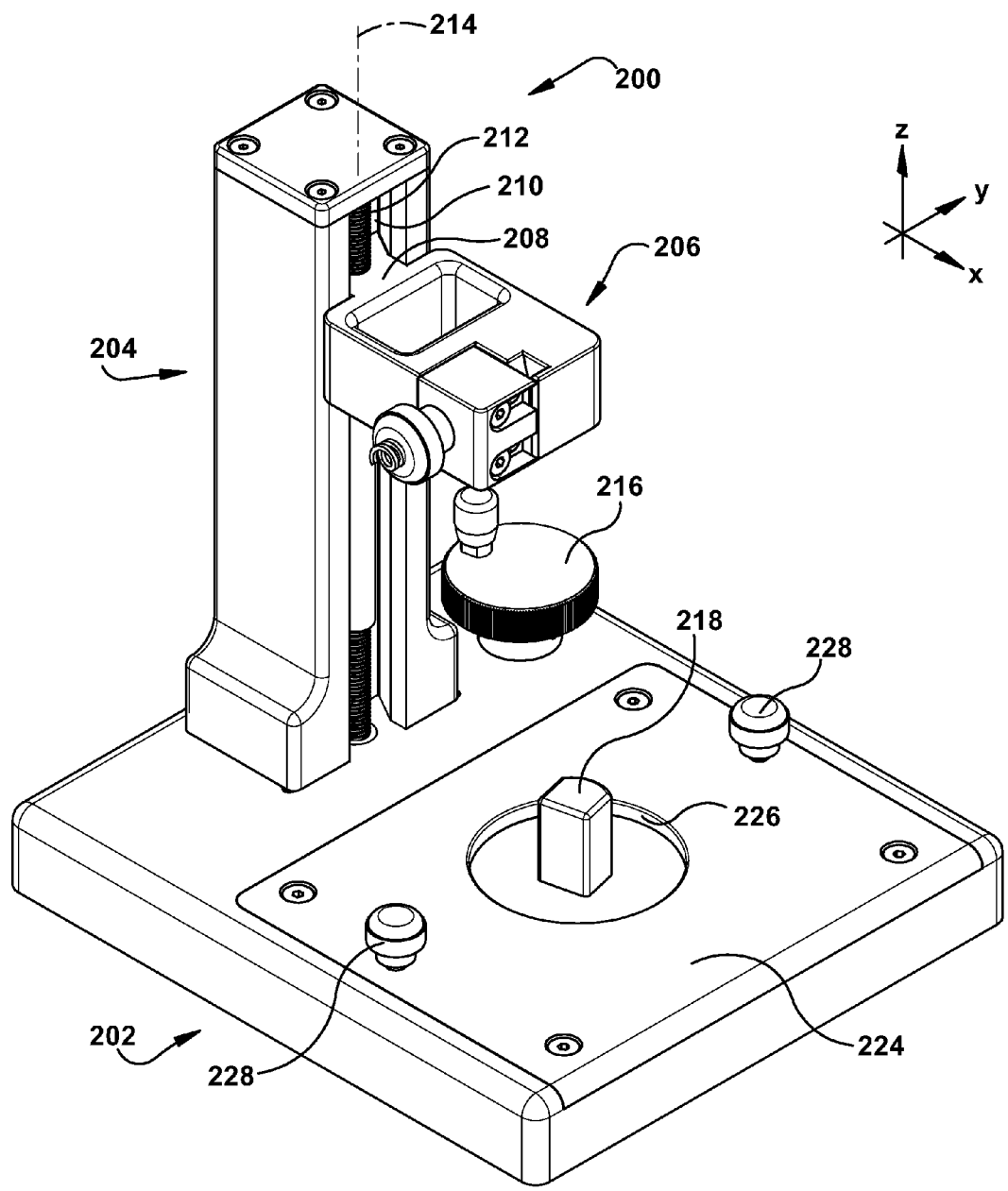
FIG. 2 is a perspective side view of an embodiment of the present invention.

FIG. 2 depicts an apparatus 200 for transferring predetermined spatial positioning information to an adjustable tool (not shown in this Figure). The apparatus 200 includes a base 202 and an elongate column 204 extending longitudinally upward from the base. A tool grasper 206 is attached to the elongate column 204 and is configured to temporarily hold at least a carrier portion of the adjustable tool stationary in relation to the base 202. The tool grasper 206 may be spaced apart from the base 202 by at least a portion of the elongate column 204.

Figure 3:
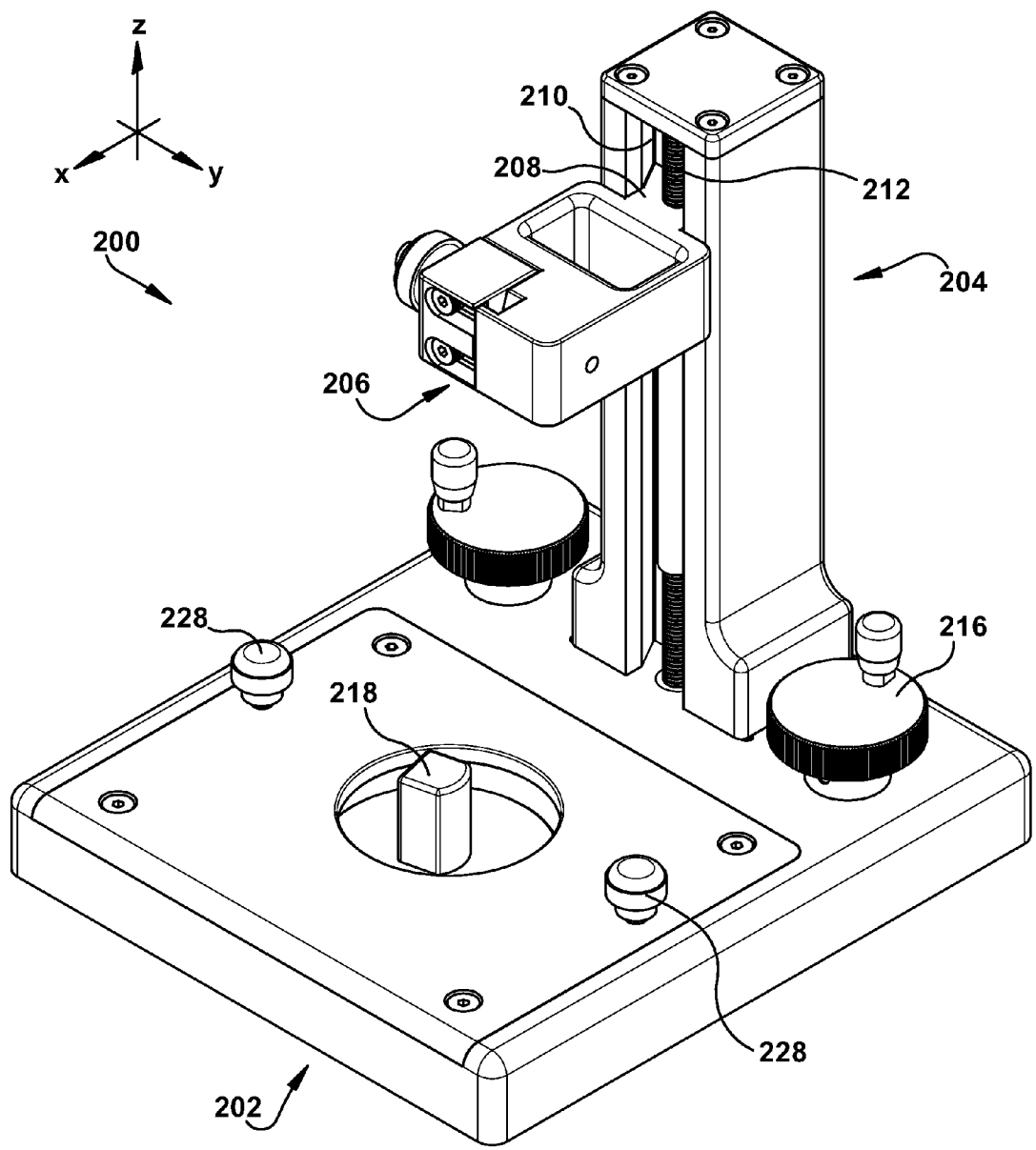
FIG. 3 is a perspective side view of the embodiment of FIG. 2.

As shown in FIGS. 2 and 3, the tool grasper 206 may be movable relative to the elongate column 206. For example, the tool grasper 206 can include a grasper protrusion 208 which is slidably engaged with a column rail 210. (While a "male" grasper protrusion 208 and "female" column rail 210 are depicted in the Figures, these structures can interact in any suitable way and are not limited to the shown arrangement.)

In the embodiment of FIGS. 1-11D, a threaded rod 212 extends longitudinally upward from the base 202 and is contained within the column rail 210. The threaded rod 212 is permitted to rotate about a longitudinal axis 214, which extends in the "Z" direction. The grasper protrusion 208 includes a threaded feature (not shown) which interacts with the threaded rod 212 to cause the tool grasper 206 to move parallel to the longitudinal axis 214 and thus up or down the elongate column 206. In this arrangement, therefore, a travel wheel 216 may be located on a user-accessible surface of the apparatus 200 (here, the base 202), so that the user can turn the travel wheel 216 to cause longitudinal (Z-axis) motion of the tool grasper.

Figure 4:
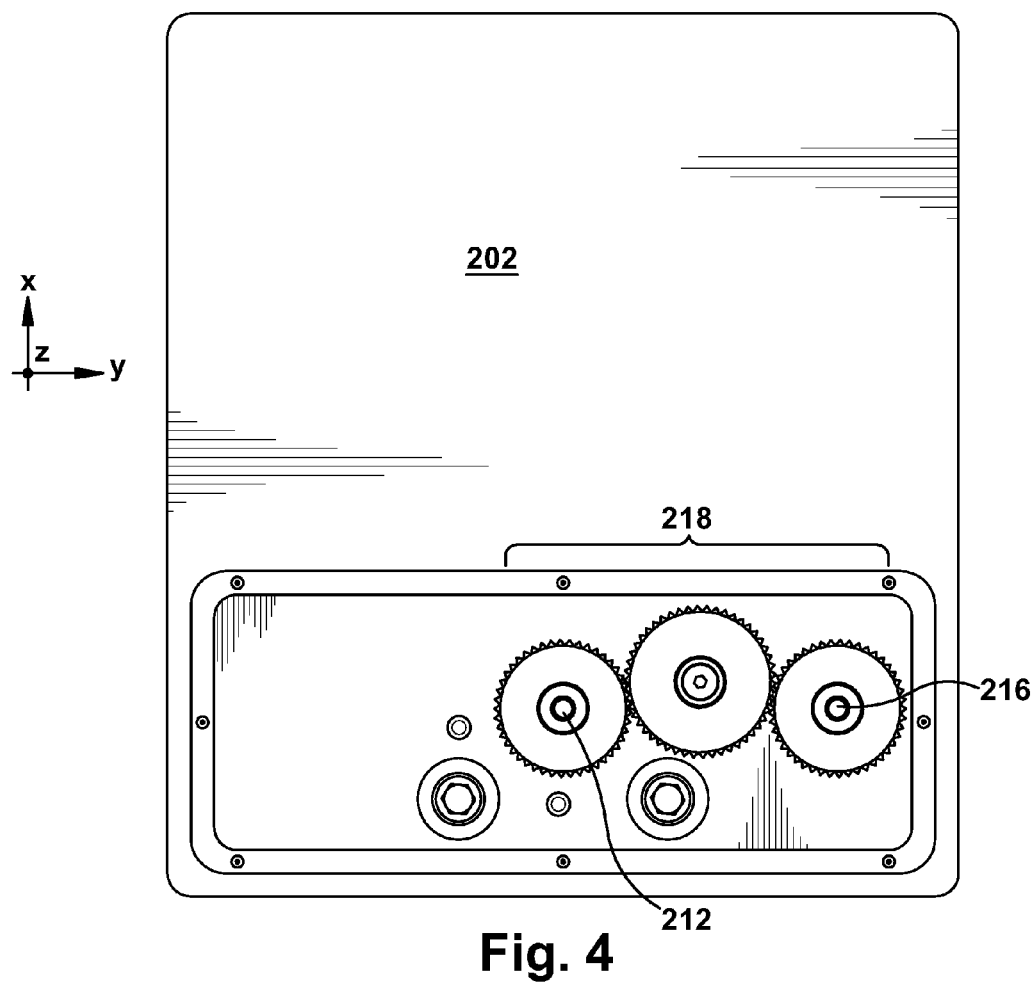
FIG. 4 is a bottom view of the embodiment of FIG. 2.

As shown in the bottom view of FIG. 4, a gear train 218 may be used to mechanically link the threaded rod 212 (or a gear or other structure attached thereto) with the travel wheel 216 (or a gear or other structure attached thereto) to transfer the user-input force from the travel wheel to turn the threaded rod and thereby adjust a height of the tool grasper 206 above the base 202 into a desired tool grasper elevation. For the depicted arrangement, it is contemplated that the force required to overcome inertia and cause the tool grasper 206 to move is high enough that the tool grasper will stay at the desired tool grasper elevation until/unless a sufficiently high user input force is exerted on the travel wheel 216. However, if desired, a brake, lock, or other holding mechanism (not shown) may be provided to help maintain the tool grasper 206 in the desired tool grasper elevation.

Though a geared arrangement is depicted for moving the tool grasper 206 longitudinally with respect to the elongate column 204 in the embodiment of FIGS. 1-11D, one of ordinary skill in the art would be able to provide any desired other means for moving the tool grasper and/or maintaining the tool grasper at the desired tool grasper elevation. These other means may include a ratcheting arrangement, a frictional fit, a pulley arrangement, a gear train other than that shown, a peg-and-hole structure, or any other suitable means for moving the tool grasper and/or maintaining the tool grasper at the desired tool grasper elevation.

The apparatus 200 may include a positioning boss 218 which protrudes from the base 202 and is configured to engage with a reference surface, as will be detailed below. When present, the positioning boss 218 may be located in any suitable position on the base 202 and may be movable with respect to the elongate column 204.

Figure 5:
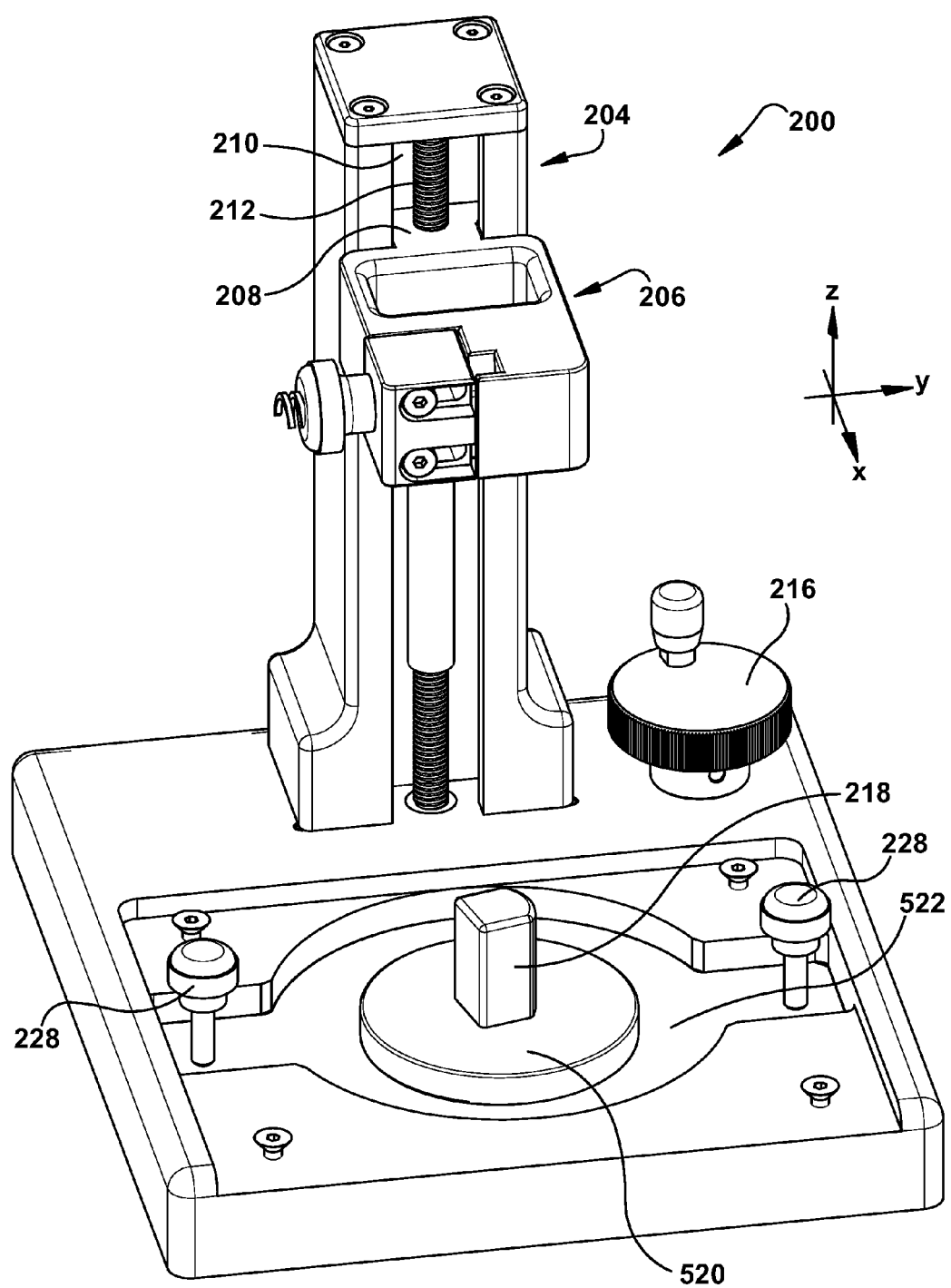
FIG. 5 is a partial perspective top view of the embodiment of FIG. 2.

One example of a suitable movement/securement mechanism for the positioning boss 218 is shown in FIG. 5. Here, the positioning boss is attached to a positioning disc 520, which may be placed in any desired location with respect to the elongate column 204 upon a base recess 522. A cover plate 224 (shown in place in FIG. 2 and omitted from FIG. 5) includes a plate aperture 226 which allows the positioning boss 218 to extend through the cover plate 224. The plate aperture 226 is contemplated to be smaller in the X-Y plane than the X-Y dimension of the positioning disc 520, so that the cover plate 224 constrains the positioning disc from longitudinal (Z-axis) motion when the apparatus 200 is assembled as shown in FIG. 2. (It should be noted that the rounded aspect of at least one of the positioning disc 520 and the base recess 522 may be helpful in allowing the positioning boss 218 to move in the yaw direction—that is, rotated about the Z-axis—as desired.) The cover plate 224 is shown here as fully removed from the apparatus 200 in FIG. 5, but one of ordinary skill in the art will recognize that the cover plate 224 may remain attached to the base 202 during placement of the positioning disc 520 in the desired location.

Optionally, if it is desirable to also constrain the positioning disc 520 (and the attached positioning boss 218) from sliding motion in the X-Y plane, at least one tightening mechanism 228 (shown here as a pair of screw-down bolts) may be provided. Once the user has placed the positioning boss 218 into the desired location with respect to the elongate column 204, the tightening mechanism 228 may be actuated to sandwich the positioning disc 520 between the cover plate 224 and the bottom of the base recess 522. Friction exerted upon the positioning disc 520 by the cover plate 224 and/or the bottom of the base recess 520 will then constrain motion of the positioning disc 520 in the X-Y plane.

FIGS. 6-8B depict various views of a patient-specific spacing block 630 which may be supported by the base 202. The spacing block 630 includes a reference surface 632 embodying predetermined spatial positioning information to be transferred to a functional portion of the adjustable tool, as will be discussed below. Because the spacing block 630 includes at least one patient-specific feature, the spacing block may be considered to be a "surrogate model", representing some aspect of the native (either original or previously altered) patient tissue in a form that can be manipulated and/or interacted with by the user.

Figure 6:
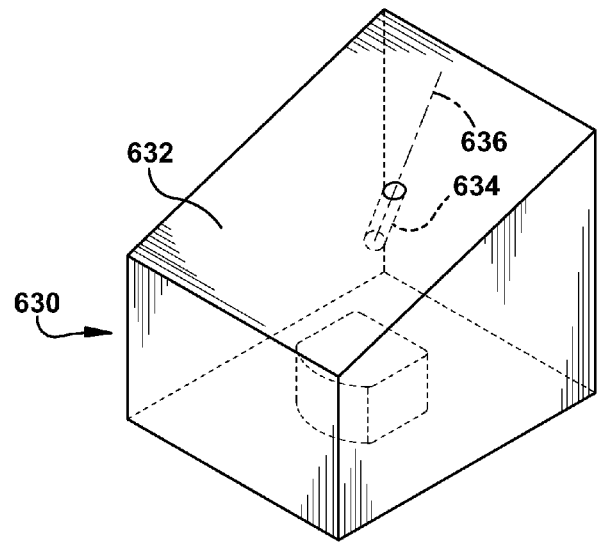
FIG. 6 is a schematic perspective view of a surrogate model for use with the embodiment of FIG. 2.

FIG. 6 depicts a schematic perspective view of a spacing block 630. Reference surface 632 of the spacing block 630 is a physical embodiment of some type or amount of predetermined spatial positioning information which could be helpful to the user in performing a specific surgical task, and therefore which is desirable to be transferred to the adjustable tool. For example, the orientation of the reference surface 632 in space, with relation to some known landmark, may represent the predetermined spatial positioning information. As another example, a reference structure 634 may be provided to embody at least a portion of the predetermined spatial positioning information. Here, the reference structure 634 is an aperture having a predetermined location upon the spacing block 630 and a predetermined trajectory 636 with respect to the reference surface 632. It is contemplated that the reference structure 634 may be any suitable structure for conveying appropriate predetermined spatial positioning information to the user such as, but not limited to, a recess or cavity in the spacing block 630, a protrusion outward from a remaining portion of the spacing block 630, and a portion of the spacing block having a discernable (e.g., visually or tactilely different, such as an embedded colored indicator) differentiation from a remaining portion of the spacing block. While the spacing block 630 shown in FIGS. 6-8B is substantially rectilinear in form, any suitable spacing block format or shape could be used, such as, but not limited to, a spacing block which replicates the three-dimensional shape of at least a portion of a patient's native anatomy as discussed below.

Figure 7:
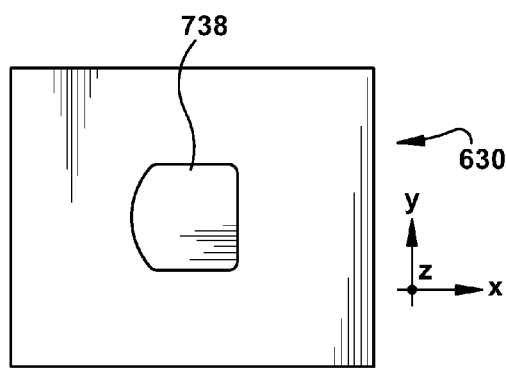
FIG. 7 is a schematic bottom view of the surrogate model of FIG. 6.

FIG. 7 is a schematic bottom view of the spacing block 630 which shows a positioning aid 738 embodied in the spacing block. Here, the positioning aid 738 is a recess or cavity in a bottom surface of the spacing block 630 which has a D-shaped silhouette in the X-Y plane. In the embodiment of FIGS. 1-11D, the positioning aid 738 is a first positioning aid. At least one of the base 202, the elongate column 204, and the tool grasper 206 includes a second positioning aid, which is represented by the positioning boss 218 in the apparatus 200 of FIGS. 1-11D. The first positioning aid 738 and second positioning aid (hereafter referenced as positioning boss 218) are configured for mutual engagement to place the spacing block 630 into a predetermined relationship with the tool grasper 206 and thereby generate a pre-set reference surface 632.

The term "pre-set" is used herein to indicate a reference surface 632 which has already been placed in a desired predetermined location and orientation in space with respect to an adjustable tool held by the tool grasper 206. A pre-set reference surface 632 may be pre-set by the configuration of the spacing block 630 which includes the reference surface, and/or may be pre-set with the assistance of one or more of the tool grasper 206 and the positioning boss 218. For example, the tool grasper 206 may be moved longitudinally with respect to the elongate column 204—as previously discussed—into a desired position, the tool grasper 206 may grasp an adjustable tool (as discussed below) in a particular manner, and/or the positioning boss 218 may be moved in any fashion, as previously discussed (whether or not the positioning boss 218 is "locked" into place via a cover plate 224), and the final position of any of these structures may be used to help "pre-set" the reference plane 632.

A chosen one of the first and second positioning aids (here, the positioning boss 218, acting as the second positioning aid) may include a protruding "male" engagement component (here, the body of the positioning boss). The other one of the first and second positioning aids (here, the first positioning aid 738) may include a receding "female" engagement component (here, the cavity in the spacing block 630). It should be noted that the male and female engagement components could be reversed, such that the spacing block 630 includes a male engagement component and the base 202 includes a female engagement component. The male and female engagement components then may, when engaged, cooperatively help place the spacing block 630 into the desired predetermined relationship with the tool grasper 206.

Figure 8A:
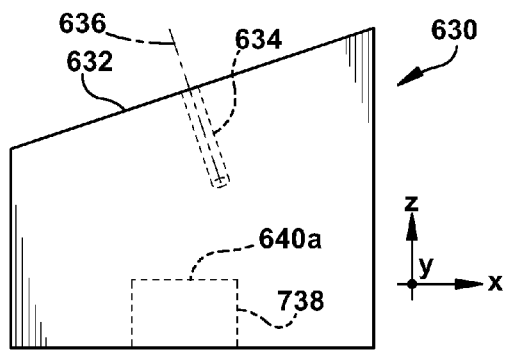
FIGS. 8A and 8B are schematic side views of optional configurations of the surrogate model of FIG. 6.
Figure 8B:
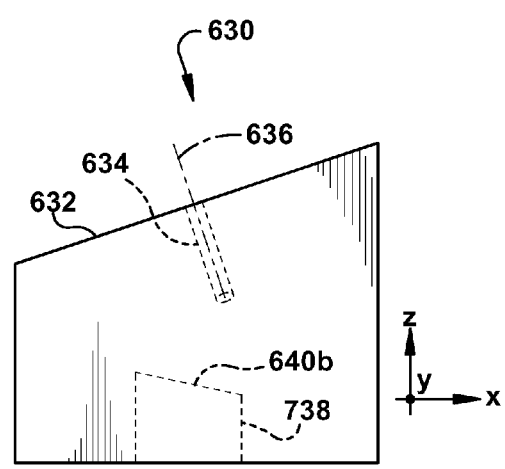

FIGS. 8A and 8B are schematic side views of optional configurations of the spacing block 530 which show two alternates for the shape of the first positioning aid 738 in the X-Z plane. In FIG. 8A, the first positioning aid 738 has a blind end 640a which is substantially parallel to the bottom surface of the spacing block 530 and thus provides a standardized foundation for engagement with the positioning boss 218. In FIG. 8B, the first positioning aid 738 has a bespoke, patient-specific blind end 640b, which is angled with respect to the bottom surface of the spacing block 530 and thus provides a patient-specific foundation for engagement with the positioning boss 218. In other words, when the first positioning aid 738 of FIG. 8B is engaged with the positioning boss 218, contact between the patient-specific blind end 640b and the top of the positioning boss 218 will tilt or cant the spacing block 630 in a predetermined manner and thereby embodies predetermined spatial positioning information in addition to, or instead of, the predetermined spatial positioning information represented by the reference surface 632.

It is also contemplated that the positioning boss 218 may also or instead include some patient-specific aspects and engage with any type of first positioning aid 738 in such a way as to transfer some predetermined spatial positioning information to the spacing block 630. This may be accomplished, for example, by making the positioning disc 520 and attached positioning boss 218 readily removable and replaceable with a different, patient-specific positioning disc 520 and attached positioning boss 218. The predetermined spatial positioning information embodied in a patient-specific first positioning aid 738 and/or second positioning aid may be transferred to the adjustable tool via operation of the apparatus 200 in the below-described manner.

The predetermined spatial positioning information may be any type of information which may be helpful in positioning the reference surface 632 and/or a reference structure 634 (which may or may not be associated with a reference surface) in at least one degree of freedom relative to a stationary frame of reference. As shown in FIG. 1, the reference surface 632 and/or reference structure 634 may be moved in space as desired in one or more of X-axis motion, Y-axis motion, Z-axis motion, pitch motion, yaw motion, and roll motion. Using the apparatus 200 of FIGS. 1-11D as an example, a patient-specific spacing block 630 may be provided and arranged with respect to a (relatively stationary) base 202 or elongate column 204 to generate the aforementioned pre-set reference surface 632, optionally with the assistance of a user-manipulable positioning boss 218 and/or tool grasper 206.

Figure 9A:
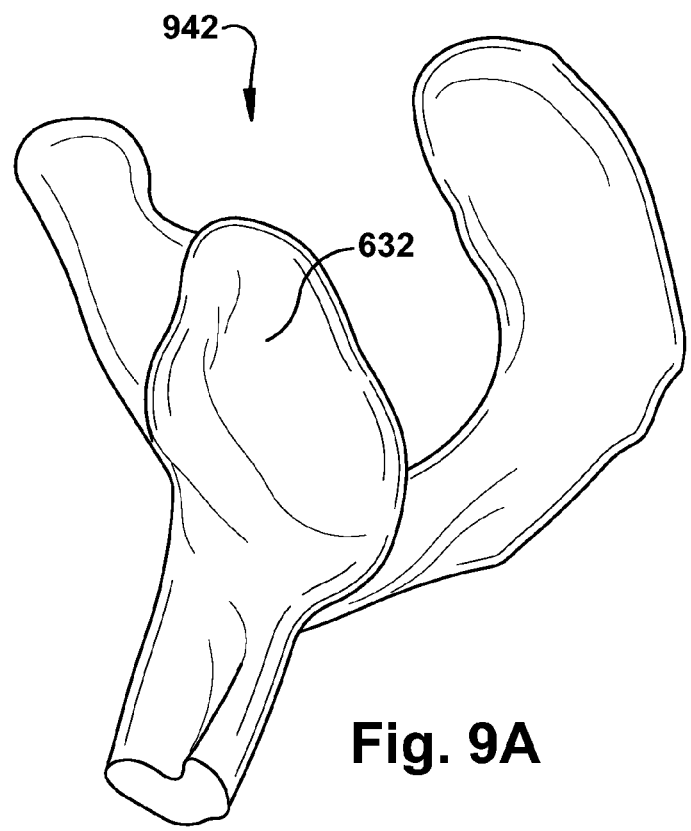
FIG. 9A is a top perspective view of a surrogate model for use with the embodiment of FIG. 2.
Figure 9B:
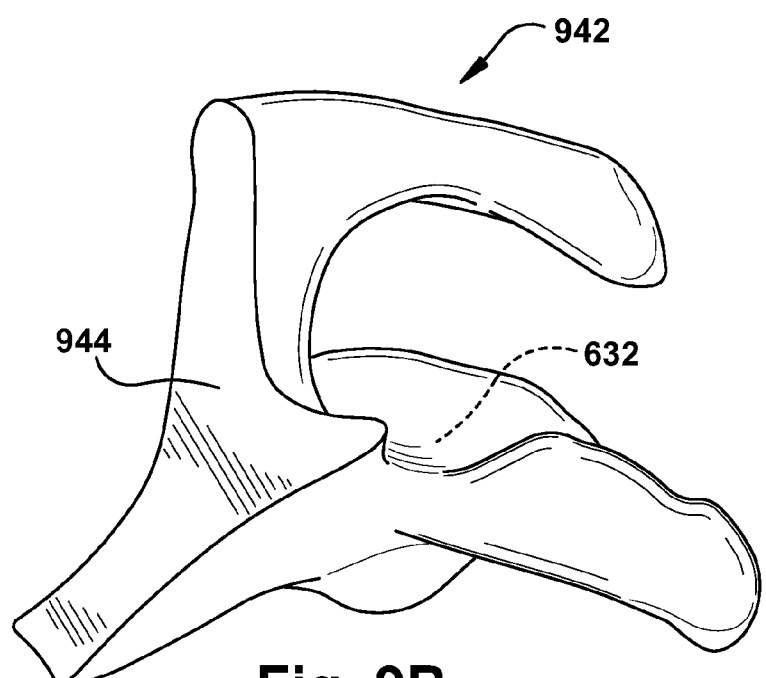
FIG. 9B is a bottom perspective view of a surrogate model for use with the embodiment of FIG. 2.

Turning now to FIGS. 9A and 9B, two views of an example of another type of patient-specific spacing block 630a are shown. The spacing block of FIGS. 9A and 9B is a surrogate model which directly represents some aspect of a patient tissue which will be revealed to direct view during a surgical procedure. An example of a suitable surrogate model is shown in co-pending U.S. Provisional Patent Application No. 61/408,392, filed Oct. 29, 2010 and titled "System of Preoperative Planning and Provision of Patient-Specific Surgical Aids", incorporated herein by reference. The patient tissue is shown and described herein at least as a scapula, but the patient tissue could be any desired type such as, but not limited to, hip joints, shoulder joints, knee joints, ankle joints, phalangeal joints, metatarsal joints, spinal structures, long bones (e.g., fracture sites), or any other suitable patient tissue use environment for the present invention. To differentiate the patient-specific spacing blocks of FIGS. 9A and 9B from the patient-specific spacing blocks 630 of FIGS. 6-8A, the former will be referenced herein as patient-specific bone models 942. (It is contemplated, however, that any patient tissue, not just bone, could be represented in the surrogate model manner described herein.)

The bone model 942 of the native patient tissue may be based upon, for example, scanned image data taken from an imaging scan of the native patient tissue. The term "model" is used herein to indicate a replica or copy of a physical item, at any relative scale and represented in any medium, physical or virtual. The bone model 942 may be a total or partial model of a subject patient tissue, and may be created in any suitable manner. For example, and as presumed in the below description, the bone model 942 may be a physical model based upon computer tomography ("CT") data imported into a computer aided drafting ("CAD") system and manufactured by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process. Additionally or alternatively, the bone model 942 may be based upon digital or analog radiography, magnetic resonance imaging, or any other suitable imaging means.

It should be noted that the bone model 942 includes a reference surface 632—here, a glenoid surface. As can be seen with reference to a bottom surface 944 of the bone models 942 (shown in FIG. 9B), the bone model includes a patient-specific bottom surface 944, which has been configured to embody predetermined spatial positioning information which can be transferred to the adjustable tool and/or provided to the user for visualization purposes.

As an example, the patient-specific bottom surface 944 of the bone model 942 may, when placed upon a table or other "ground" surface, provide the surgeon with information about the orientation and arrangement of the native patient tissue that the user will encounter when the surgical wound. It is difficult to place a patient upon the operating table such that their native tissue is at a predetermined or precise viewing/access orientation, particularly when the native tissue (e.g., the scapula) exhibits a nonstandard anatomical configuration or when landmarks on the native tissue are difficult to discern within the surgical wound. However, the user can "airplane" or tilt the operating table to place the patient's glenoid surface into a desired orientation, which may be chosen to substantially match the orientation that the bone model 942 achieves when the patient-specific bottom surface 944 is placed on a non-tilted table or other "ground" surface. In this manner, the bone model 942 can serve as a real-time reference during surgery and one of ordinary skill in the art can readily envision the position, size, orientation, or any other characteristic of the native patient bone—which could be at least partially obstructed by surrounding tissue at the surgical site—by reference to the bone model.

As another example, the patient-specific bottom surface 944 of the bone model 942 may, when placed upon a table or other "ground" surface, provide the surgeon with a spatial reference having a predetermined orientation with remaining portions of the patient's natural anatomy. For example, the patient-specific bottom surface 944 could hold the glenoid surface in a desired orientation (e.g., perpendicular) with the scapular plane (or another convenient reference plane) when the bone model 942 is resting on a table, through selection/use of the patient-specific bottom surface. This or similar "spatial orientations" embodied in the bone model 942 may help the user to more intuitively understand the severity of the pathology by seeing how much the patient's tissue deviates from a "normal" or expected spatial arrangement. Additionally, the bone model 942 can provide the user with a "landmark" (as will be described below), and a user can view the relationship between the bone model and the landmark—optionally with the aid of a "spatial orientation" feature—to determine the nature and extent of tissue modifications that may be desired during the surgery.

Optionally, patient information, such as a name or other identifying information could be molded or machined into, inscribed upon, or otherwise associated with the bone model 942 or other spacing block 630. The spacing block 630 of FIGS. 6-8B could also be created and/or manufactured in any of the ways described above for the bone model 942, or in any other suitable manner. For simplicity, the remainder of this description will use the term "spacing block" and the element number 630 to reference a bone model 942, as shown in FIG. 9, a spacing block as shown in FIGS. 6-8B, or any other suitable spacing block, whether or not visually representative of an actual patient tissue, which a user may find helpful in transferring predetermined spatial positioning information to an adjustable tool.

Figure 10:
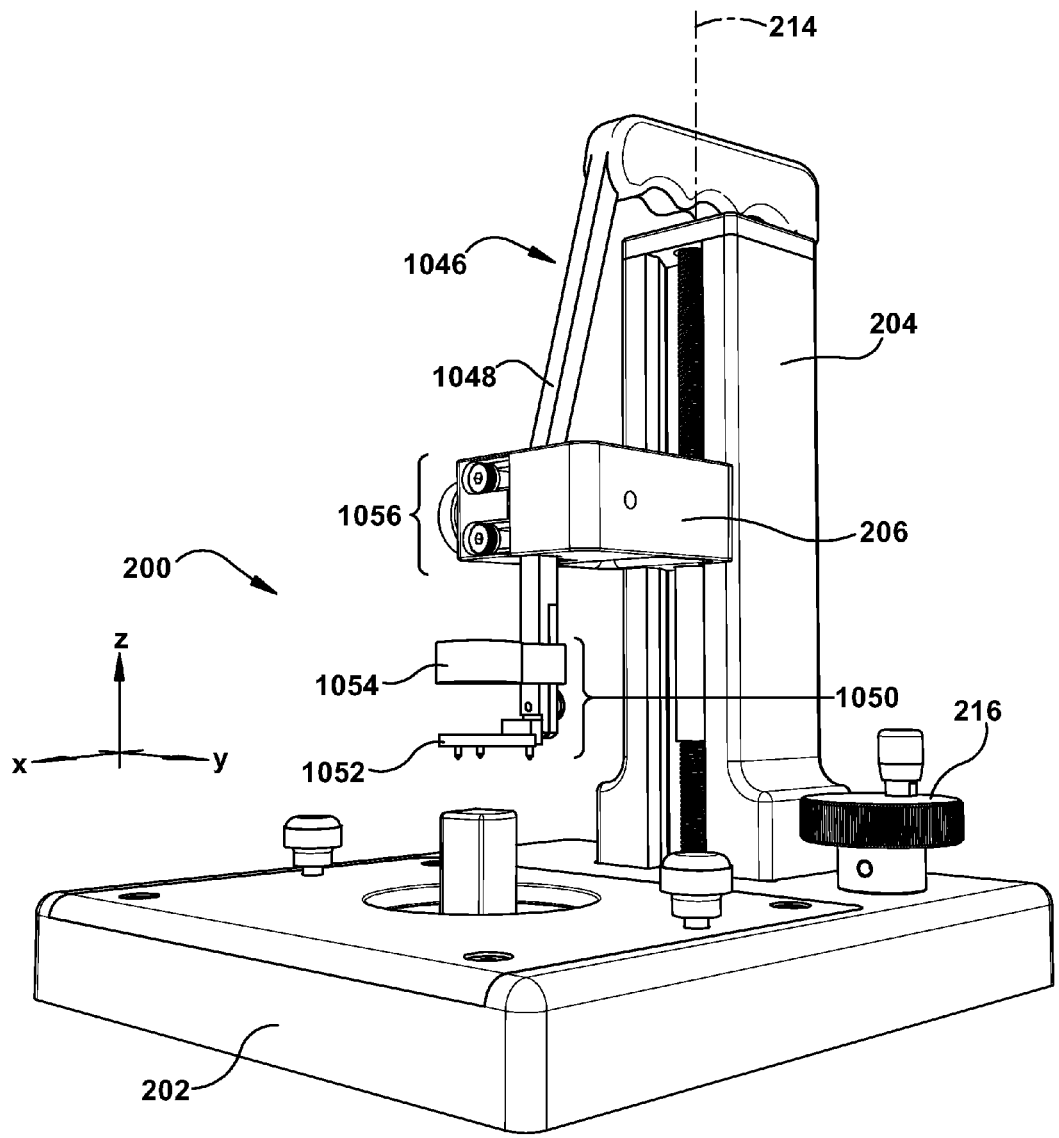
FIG. 10 is a perspective side view of the embodiment of FIG. 2 in a first use arrangement.

FIG. 10 depicts the apparatus 200 engaged with an adjustable tool 1046 such as that disclosed in co-pending U.S. patent application Ser. No. 12/854,362, filed Aug. 11, 2010 and titled "Method and Apparatus for Insertion of an Elongate Pin into a Surface", previously incorporated by reference. The adjustable tool 1046 includes a carrier portion, discussed herein as handling rod 1048, and a functional portion 1050, which includes trajectory structure 1052 and location structure 1054. Location structure 1054 is slidably attached to handling rod 1048 for longitudinal movement with respect thereto, and the location structure may be locked into a desired orientation with respect to the handling rod. Trajectory structure 1052 is attached to handling rod 1048 in a pivoting or "wristed" manner, for selective movement with respect thereto, and the trajectory structure may be locked into a desired orientation with respect to the handling rod.

The tool grasper 206 of the apparatus 200 may include at least one clamping feature 1056, of any suitable type, configured to releasably hold at least the carrier portion (here, the handling rod 1048) of the adjustable tool 1046 stationary relative to the elongate column 204. Here, the clamping feature 1056 includes a mechanical arrangement configured to accept a portion of the handling rod 1048 and close upon that portion of the handling rod, under control of a user (e.g., the user turns a manipulable wheel or lever on the clamping feature to engage the handling rod), but one of ordinary skill in the art could readily provide a suitable clamping feature 1056 to releasably hold some portion of the adjustable tool 1046 stationary relative to the elongate column 204.

For example, and as shown in FIG. 10, the user can turn the travel wheel 216 (or any other means for translating the tool grasper 206 along the longitudinal axis 214) until the tool grasper 206 reaches a predetermined location with respect to the elongate column 204. This location may be predetermined by the user and/or by an external dictator, such as, but not limited to, a preoperative planning system such as that disclosed in co-pending U.S. Provisional Patent Application No. 61/408,392, filed Oct. 29, 2010 and titled "System of Preoperative Planning and Provision of Patient-Specific Surgical Aids", incorporated herein by reference in its entirety. The handling rod 1048 or another suitable structure (which will usually, but not always, be a carrier portion) of the adjustable tool 1046 is temporarily held stationary relative to the elongate column 204 and, by extension, the base 202 of the apparatus 200, such as by engagement of the handling rod 1048 with the clamping feature 1056. The apparatus 200 and adjustable tool 1046 then achieve the arrangement shown in FIG. 10.

Before, during, and/or after association of the apparatus 200 with the adjustable tool 1046 into the FIG. 10 arrangement, the spacing block 630 (here, a bone model 942 referenced as a "spacing block 630" under the convention previously established) may be placed upon the apparatus 200, as shown in FIGS. 11A-11D. While a rectilinear, nonrepresentative spacing block may also or instead be used in a similar configuration to that of FIGS. 11A-11D, a patient-specific bone model, such as that shown in FIGS. 9A and 9B, is shown in these Figures. The spacing block 630, and the various surfaces and features thereof, may be generated in any desired manner, such as with the assistance of the aforementioned—or any other—preoperative planning system. The spacing block 630 may be particularly helpful to physically embody reference structures, predetermined spatial positioning information, and other information which the user may wish to quickly and intuitively access during the surgical procedure.

A preoperative planning system may also or instead provide the user with predetermined settings for the adjustable portions of the apparatus 200, which may themselves be helpful in imparting predetermined spatial positioning information to the reference surface 632. In this instance, scales, detents, or other markings or structures may be provided to the apparatus 200 to assist the user with placing the movable structures of the apparatus into the appropriate predetermined positions.

Figure 11A:
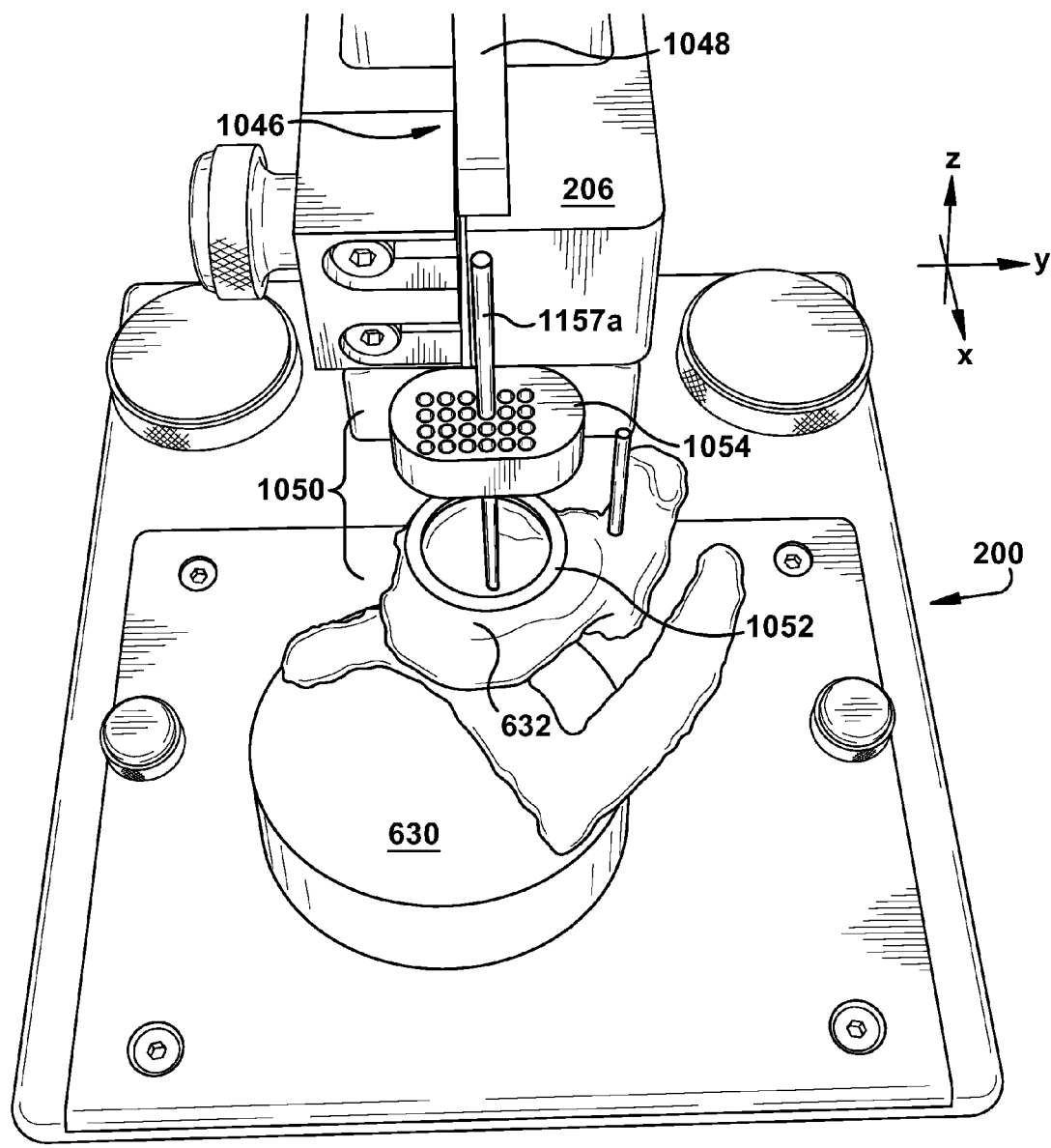
FIG. 11A is a partial perspective view of the embodiment of FIG. 2 in the first use arrangement in combination with the surrogate model of FIGS. 9A-9B.
Figure 11B:
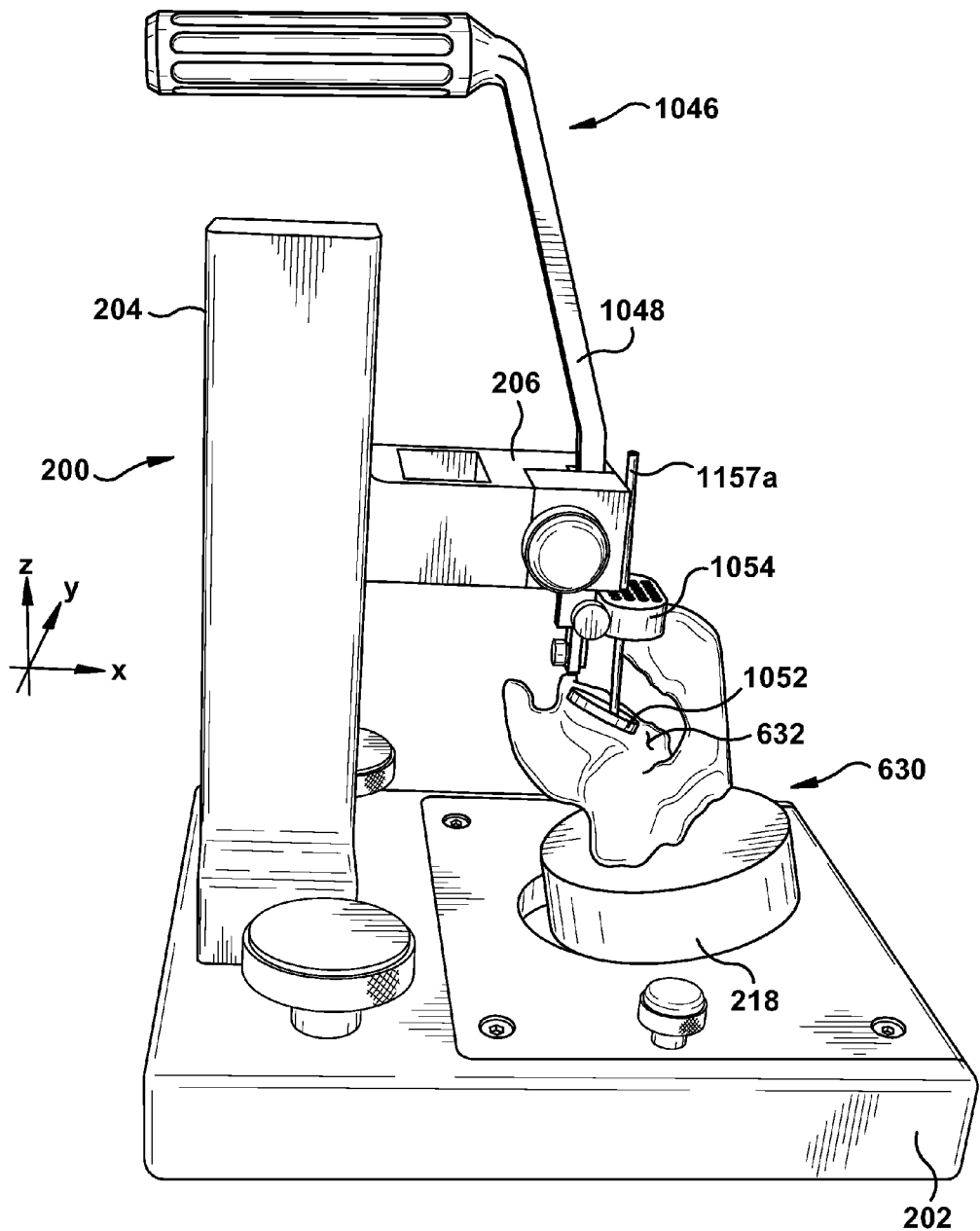
FIG. 11B is a side view of the embodiment of FIG. 2 in the first use arrangement in combination with the surrogate model of FIGS. 9A-9B.

In FIGS. 11A-11D, the positioning boss 218 has been placed into a desired location and orientation relative to the elongate column 204, optionally as described above with reference to the cover plate 224 and plate aperture 226. The first positioning aid 738 of the spacing block 630 has been mated with the positioning boss 218. When the first positioning aid 738 includes a blind end 640b which, itself, communicates some predetermined spatial positioning information, interaction between the first positioning aid and the positioning boss 218 may tilt the spacing block 630 in at least one degree of freedom, chosen from X-axis, Y-axis, Z-axis, pitch, yaw, and roll. For example, and as can be seen in FIG. 11B, the spacing block 630 does not sit squarely upon the first positioning aid 738 but is tilted (yawed) back toward the elongate column 204. Even if the blind end 640a is of the standardized type, the location and orientation of the first positioning aid 738 upon the bottom of the spacing block 630 may impart some predetermined spatial positioning information to the reference surface 632—this option may be particularly helpful if the positioning boss 218 is fixed and immobile relative to the elongate column 204.

Once the spacing block 630 has been placed (in any suitable manner) into a predetermined location and orientation with respect to a relatively stationary portion of the apparatus 200 (e.g., the elongate column 204, the base 202, or any other suitable structure), then the reference surface 632 has been manipulated, by virtue of its placement upon, and relationship to, the spacing block, in at least one degree of freedom (X-axis, Y-axis, Z-axis, pitch, yaw, and roll). When the reference surface 632 is in the predetermined position, then the manipulations of the reference surface can be said to have generated the pre-set reference surface embodying the predetermined spatial positioning information. This is the arrangement shown in FIGS. 11A-11D.

Also in FIGS. 11A-11D, the tool grasper 206 has been translated into a predetermined location and orientation (where these are adjustable) with respect to the elongate column 204 and the clamping feature 1056 is engaged to hold the adjustable tool 1046 in a predetermined location and orientation (where these are adjustable) with respect to some other portion of the apparatus, such as the base 202 and/or the elongate column 204. Once the apparatus 200 and spacing block 630 have been manipulated to generate the pre-set reference surface 632 and the adjustable tool 1046 is held in a predetermined position with respect to the reference surface, then a functional portion 1050 of the adjustable tool may be manipulated into a predetermined setting position relative to the reference surface. This predetermined setting position is shown as having been achieved in FIGS. 11A-11D, and is reflective of the predetermined spatial positioning information. For example, a wristed trajectory structure 1052 of the adjustable tool 1046 may be manipulated until a predetermined number of points on an underside of the trajectory structure all simultaneously contact the pre-set reference surface 632, as shown.

As another example, when a reference structure 634 taking the form of a drilled hole having a predetermined location and trajectory is provided to the spacing block 630, a guide pin 1157 could be held by the reference structure. In this example, a first guide pin 1157a in the reference structure 634 shown in FIGS. 11A-11B will reflect a desired location and trajectory of a corresponding guide pin, drill bit, or other penetration into the patient tissue. The guide pin 1157a in the reference structure 634 will protrude from the reference surface 632, and the functional portion 1050 can then be adjusted—that is, the trajectory structure 1052 and/or location structure 1054 can be manipulated—until the functional portion has achieved the predetermined setting position, as shown in FIGS. 11A-11B.

More specifically, the guide pin 1157a extends through a predetermined portion of the location structure 1054. The same predetermined portion of the location structure will be used in dictating the trajectory of another pin, drill, or other penetrating structure into the patient tissue during the surgical procedure, when the adjustable tool 1046 is being used to transfer the desired location and trajectory information from the spacing block 630 to the patient tissue. Contact between the trajectory structure 1052 and a portion of the patient tissue corresponding to the portion of the reference surface 632 will help transfer the desired trajectory information from the spacing block 630 to the patient tissue. Insertion of the guide pin, drill, or other penetrating structure through the predetermined portion of the location structure 1054 will help transfer the desired location information from the spacing block 630 to the patient tissue. Thus, by using the guide pin 1157a and the adjustable tool 1046, calibrated or "set" with the assistance of a spacing block 630—which optionally is a reproduction of patient tissue structures—four degrees of freedom (here, for example, X, Y, pitch [motion about the X axis], and yaw [motion about the Y axis], in the orientation of the Figures) may be transferred from the spacing block 630 to a guide pin being inserted into the patient tissue with the aid of the adjustable tool.

An additional example of use of the present invention includes visual markings (not shown) located in a predetermined relationship with the reference surface 632, such as by being marked upon the reference surface. This example, with visual markings, may be well-suited to a spacing block 630 which is a bone model 942, as shown in FIGS. 11A-11D. When a bone model 942 is used, natural landmarks of the patient tissue may be used as the visual markings. Markings, including graduated scales, bullseyes, contour lines, or any other position indicator(s) may also or instead be placed upon the reference surface 632 to serve as landmarks (visual or otherwise) for any desired purpose. The reference surface 632 can then impart the predetermined setting position to the functional portion 1050—e.g., by setting up a predetermined angular relationship between the trajectory structure 1052 and the handling rod—and the user can duplicate in situ the position of the adjustable tool 1046 upon the spacing block 630, optionally at least partially by reference to corresponding visually or palpably apparent features on the patient tissue.

Regardless of how the functional portion 1050 achieves the predetermined setting position, that predetermined setting position is maintained (e.g., by locking structures of the functional portion 1050 into place in a desired manner) and the adjustable tool 1046 is removed from the stationary relationship with the pre-set reference surface 632 with the functional portion of the adjustable tool being maintained in the predetermined setting position as, and after, the adjustable tool is removed from the apparatus 200. The user is then left with an adjustable tool 1046 which is configured for placement on or near patient tissue which corresponds to the reference surface 632, and via the predetermined setting position, information embodied in the reference surface 632 is available to the user to be employed with the corresponding patient tissue.

Depending upon the type of predetermined spatial positioning information which is to be imparted to the adjustable tool 1046, movement may be facilitated in one, two, or more degrees of freedom (X-axis, Y-axis, Z-axis, pitch, yaw, and roll) by employment of various combinations of spacing block 630, reference surface 632, first positioning aid 738, or any other structures of the apparatus 200.

Figure 11C:
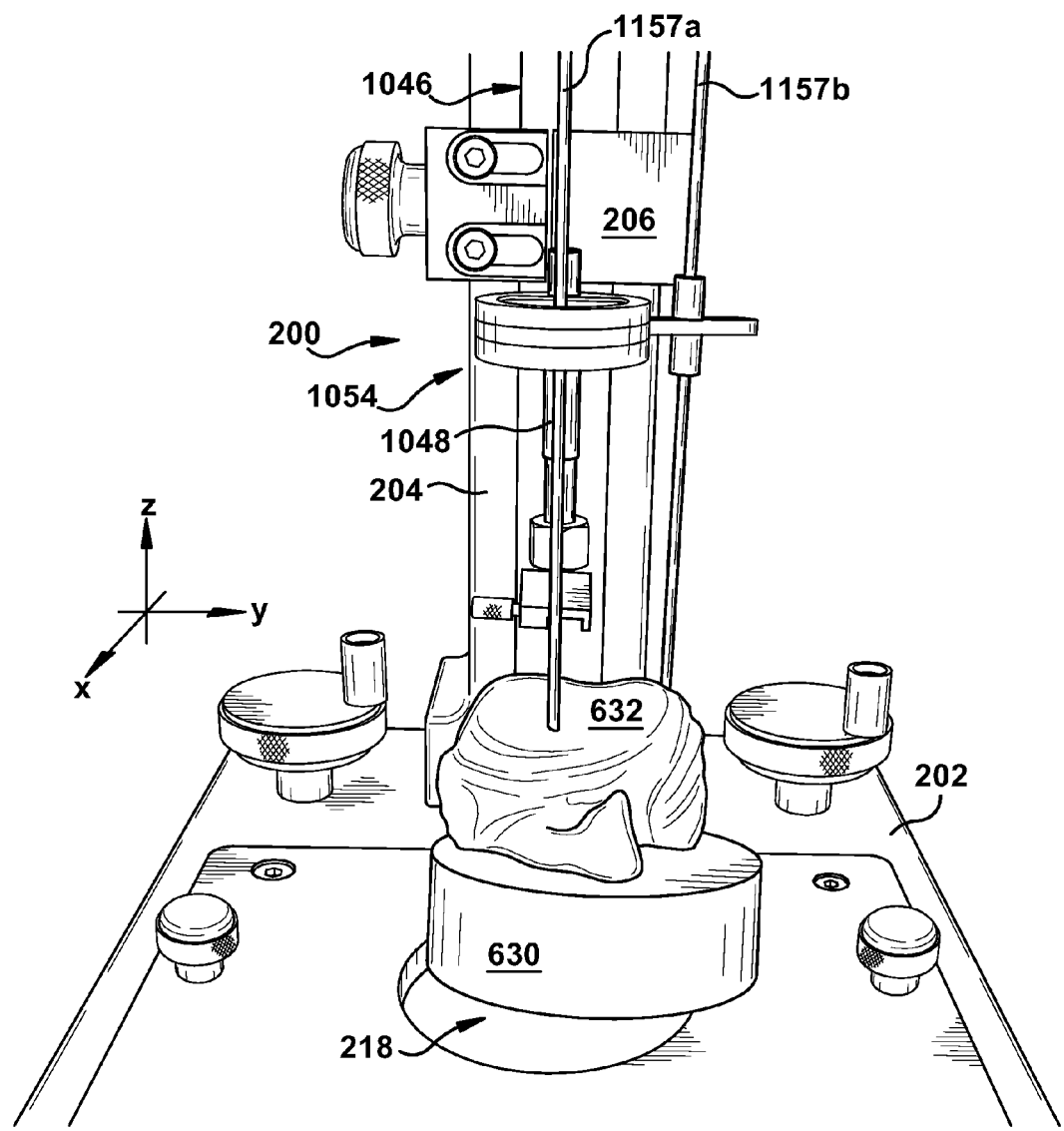
FIG. 11C is a partial perspective view of the arrangement of FIG. 11A having an alternate configuration.
Figure 11D:
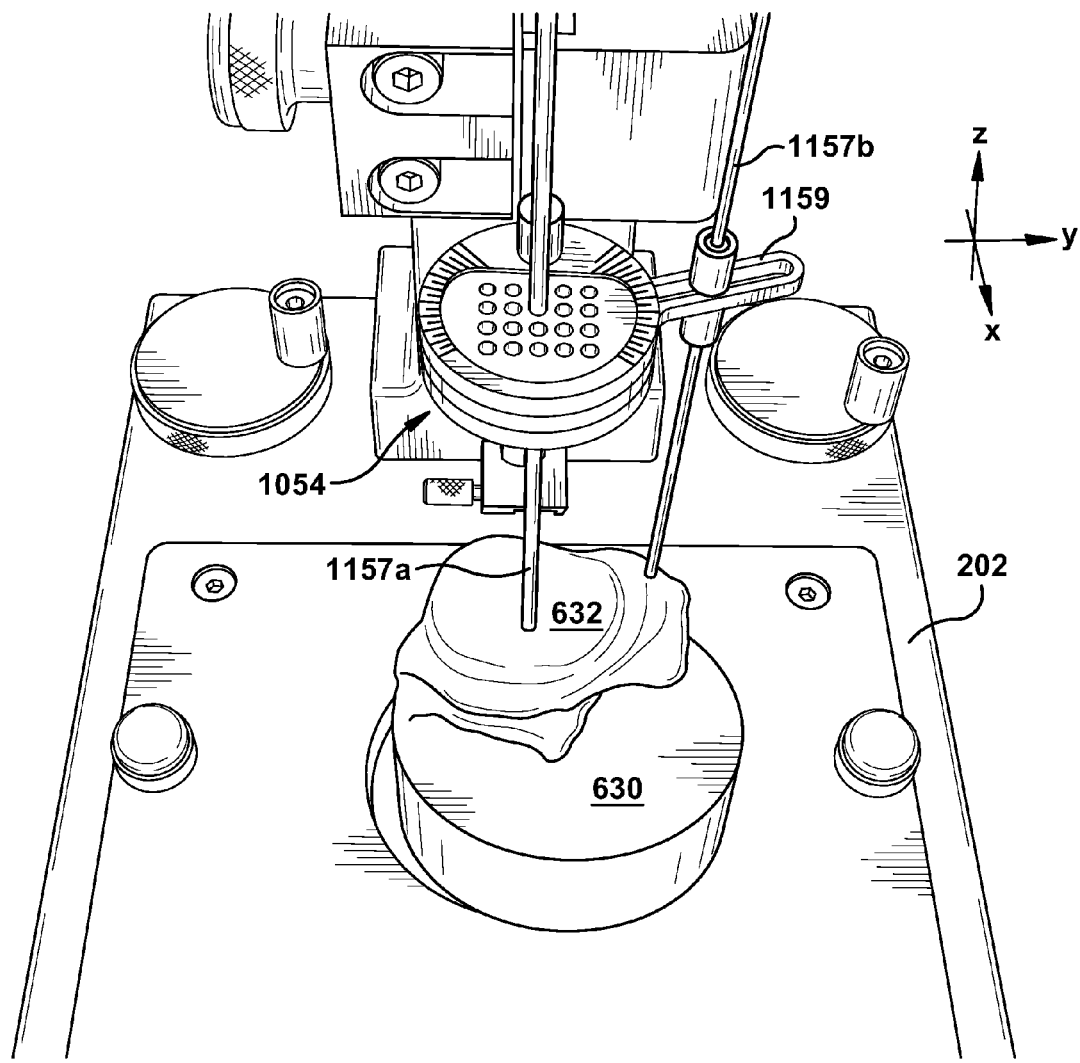
FIG. 11D is a partial perspective view of the arrangement of FIG. 11A having an alternate configuration.

FIGS. 11C-11D depict a relevant portion of an adjustable tool 1046 which can be used in guiding, imparting, and/or transferring an additional degree of freedom from the spacing block 630 to the guided pin, drill, or other penetrating structure. In FIGS. 11C-11D, an additional guide pin 1157b is located off to one side of the first guide pin 1157a (which is used to set the adjustable tool 1046 to transfer the desired location and trajectory). (It should be noted that the trajectory structure 1052 has been omitted from FIGS. 11C-11D for clarity of depiction, but that the trajectory structure 1052 will normally be present on the adjustable tool 1046 and set/used for the configuration of FIGS. 11C-11D substantially as previously described with reference to FIGS. 11A-11B.)

The additional guide pin 1157b can be used in conjunction with an adjustable protruding arm 1159 (here, including a cylindrical bushing configured to accept the guide pin 1157b). As shown in FIGS. 11C-11D, the protruding arm 1159 is movably connected to the remaining elements of the locating structure 1054 through use of a ring which can be pivoted to allow the protruding arm 1159 to extend laterally at different angles relative to the pin block of the locating structure 1054. Optionally, and as shown in FIGS. 11C-11D, a rotational scale may be provided to assist with achieving a desired angular relationship between the protruding arm 1159 and other portions of the locating structure 1054. Also optionally, a locking or detent mechanism (not shown) may be provided to help maintain the desired angular relationship between the protruding arm 1159 and other portions of the locating structure 1054.

When present, the protruding arm 1159 shown in FIGS. 11C-11D may be used in transferring the additional spatial positioning information of roll (about the Z-axis)—that is, the rotational position of guide pin 1157a relative to the reference surface 632—from the spacing block 630 to the adjustable tool for transfer to the patient tissue. In other words, the guide pin 1157a shown in FIGS. 11A-11D is substantially rotationally symmetrical and therefore agnostic as to the roll position it takes with respect to the spacing block 630. However, if the guide pin 1157a had some rotational differentiation (e.g., a flatted side, a protruding lug, or any other asymmetry), it may be important to the user to have that rotational differentiating feature "pointing" in a certain direction when a pin, drill, or other penetrating structure based upon the guide pin 1157*a* is placed at the desired location and trajectory in the patient tissue. Through use of the protruding arm 1159 and additional guide pin 1157*b*, a desired rotation can also be transferred.

The FIGS. 11C-11D arrangement results in the total spatial positioning information made available from the spacing block 630 to the adjustable tool 1046 including five (X, Y, pitch [about the X axis], yaw [about the Y axis], and roll [about the Z axis) degrees of the six possible degrees of freedom. The sixth (missing) degree of freedom—namely, Z-axis travel—can be provided to the penetrating pin, drill, or other structure through the use of a depth-indicating/controlling tool such as, but not limited to, that disclosed in co-pending U.S. Provisional Patent Application No. 61/431,472, filed Jan. 11, 2011 and titled "Distance Indicator", the entire contents of which are incorporated herein by reference. In this manner, a pin, drill, or other penetrating structure may be precisely placed in a desired location, trajectory, and/or rotational relationship with a patient tissue with the assistance of the spacing block 630, adjustable tool 1046, and/or apparatus 200.

As another use for the protruding arm 1159, the spacing block 630 could originally be provided with only the first guide pin 1157*a*. The protruding arm 1159 could then be rotated into the desired angular relationship with the other portions of the locating structure 1054, optionally with the use of a rotational scale such as that shown in FIGS. 11C-11D. Once the protruding arm 1159 has been positioned as desired to embody roll information (which is optionally predetermined with the assistance of the aforementioned or another preoperative planning system), the additional guide pin 1157*b* may be inserted through the bushing or another predetermined portion of the protruding arm 1159 and into the spacing block 630. (It is contemplated that the bushing may itself be adjustable along the protruding arm 1159 toward and away from the other portions of the locating structure 1054—optionally with the use of a length scale, not shown—to provide even greater flexibility in possible positions of the additional guide pin 1157*b* with respect to the other depicted structures.)

Through use of the protruding arm 1159 to dictate insertion location and/or trajectory of the additional guide pin 1157*b* as described, the additional guide pin 1157*b* may be used to help transfer predetermined spatial information from the adjustable tool 1046 to the spacing block 630 and/or to the patient tissue, as desired. One of ordinary skill in the art will be able to readily specify and determine which spatial information can be transferred between a spacing block 630 and a patient tissue with the use of the described systems and methods for a particular application of the present invention.

One of ordinary skill in the art, upon review of the present disclosure, will understand that it is possible to place the adjustable tool 1046 into a configuration in which the functional portion 1050 is in a predetermined setting position which is based upon a relationship between the functional portion and the reference surface 632 which may be readily duplicated between the functional portion and the actual patient tissue corresponding to the reference surface. In this predetermined setting position, the handling rod 1048 (or any other portion of the adjustable tool 1046 which is stationary relative to the functional portion 1050) will have a substantially fixed relationship to the reference surface 632. As long as the predetermined setting position is maintained when the adjustable tool 1046 is removed from the apparatus 200, the handling rod 1048 (or other relatively stationary portion of the adjustable tool) will bear the same relationship to the actual patient tissue as it did to the reference surface 632. This results in a relatively dependable scheme by which predetermined spatial positioning information may be transferred between the reference surface 632 and the actual patient tissue.

FIGS. 12-18 depict an apparatus 200' according to a second embodiment of the present invention. The apparatus 200' of FIGS. 12-18 is similar to the apparatus 200 of FIGS. 1-11B and therefore, structures of FIGS. 12-18 that are the same as, or similar to, those described with reference to FIGS. 1-11B have the same reference numbers with the addition of a "prime" mark. Description of common elements and operation similar to those in the previously described embodiment will not be repeated with respect to the variation of FIGS. 12-18.

Figure 12:
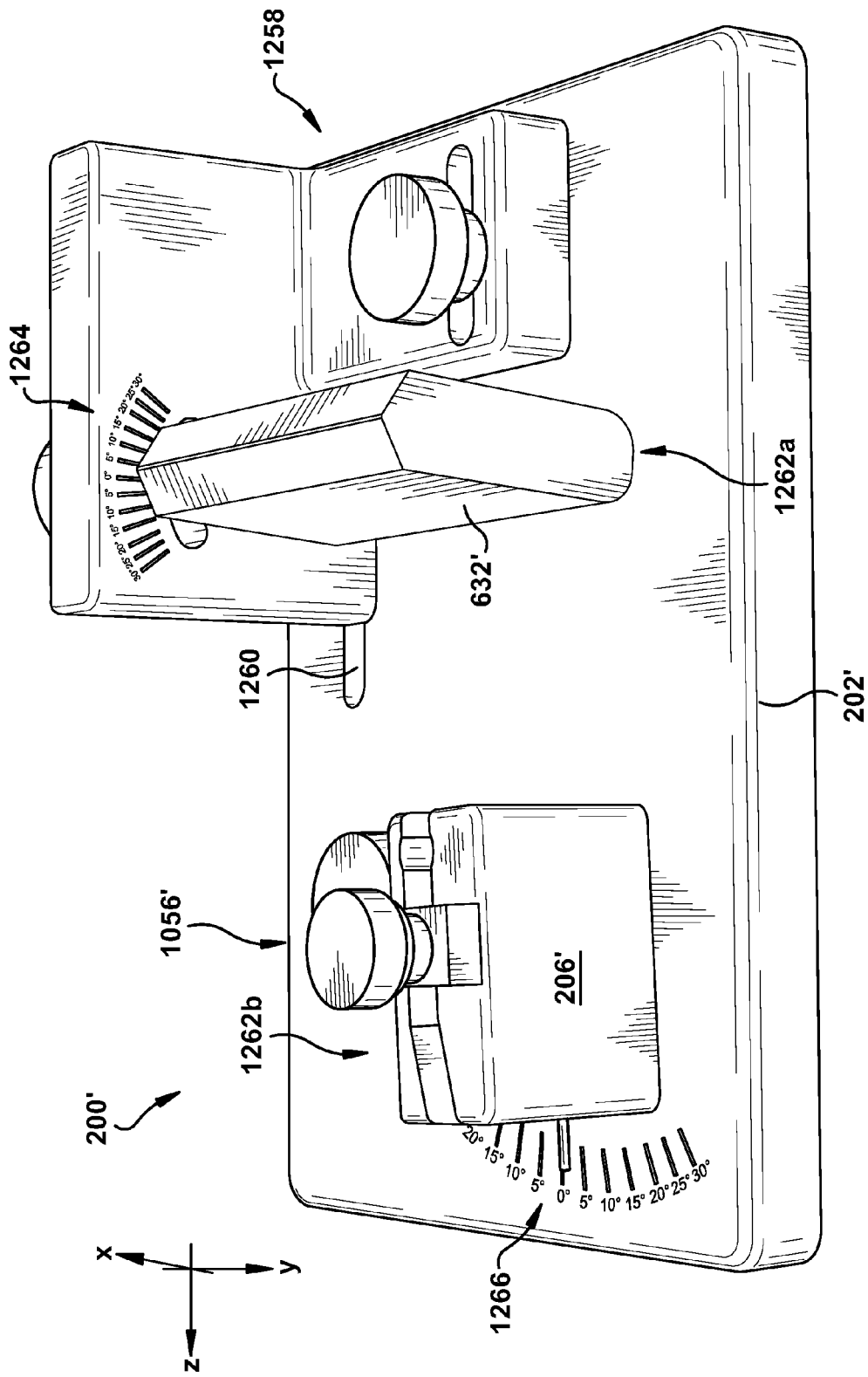
FIG. 12 is a perspective side view of an embodiment of the present invention.
Figure 13:
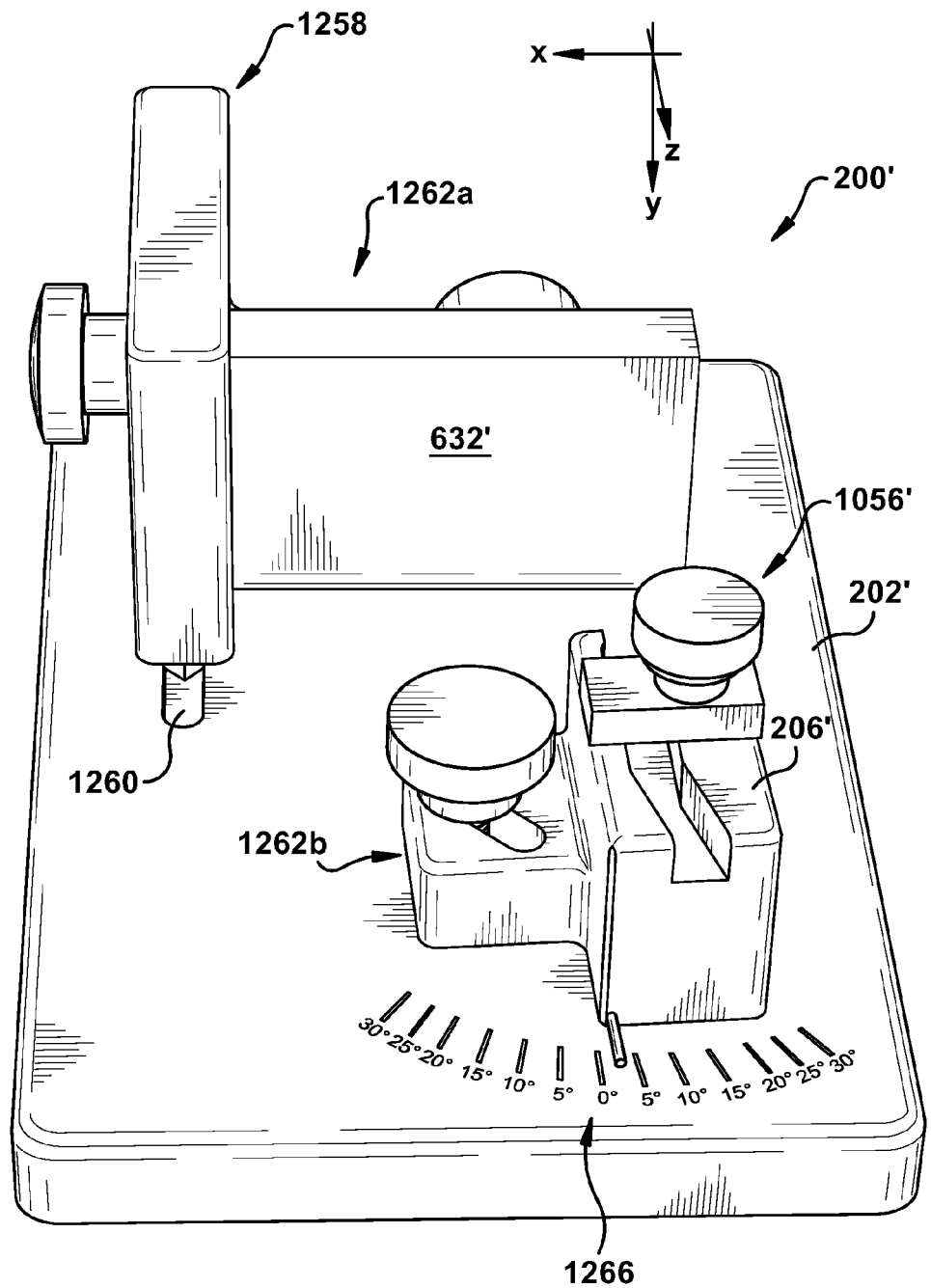
FIG. 13 is a perspective front view of the embodiment of FIG. 12.
Figure 14:
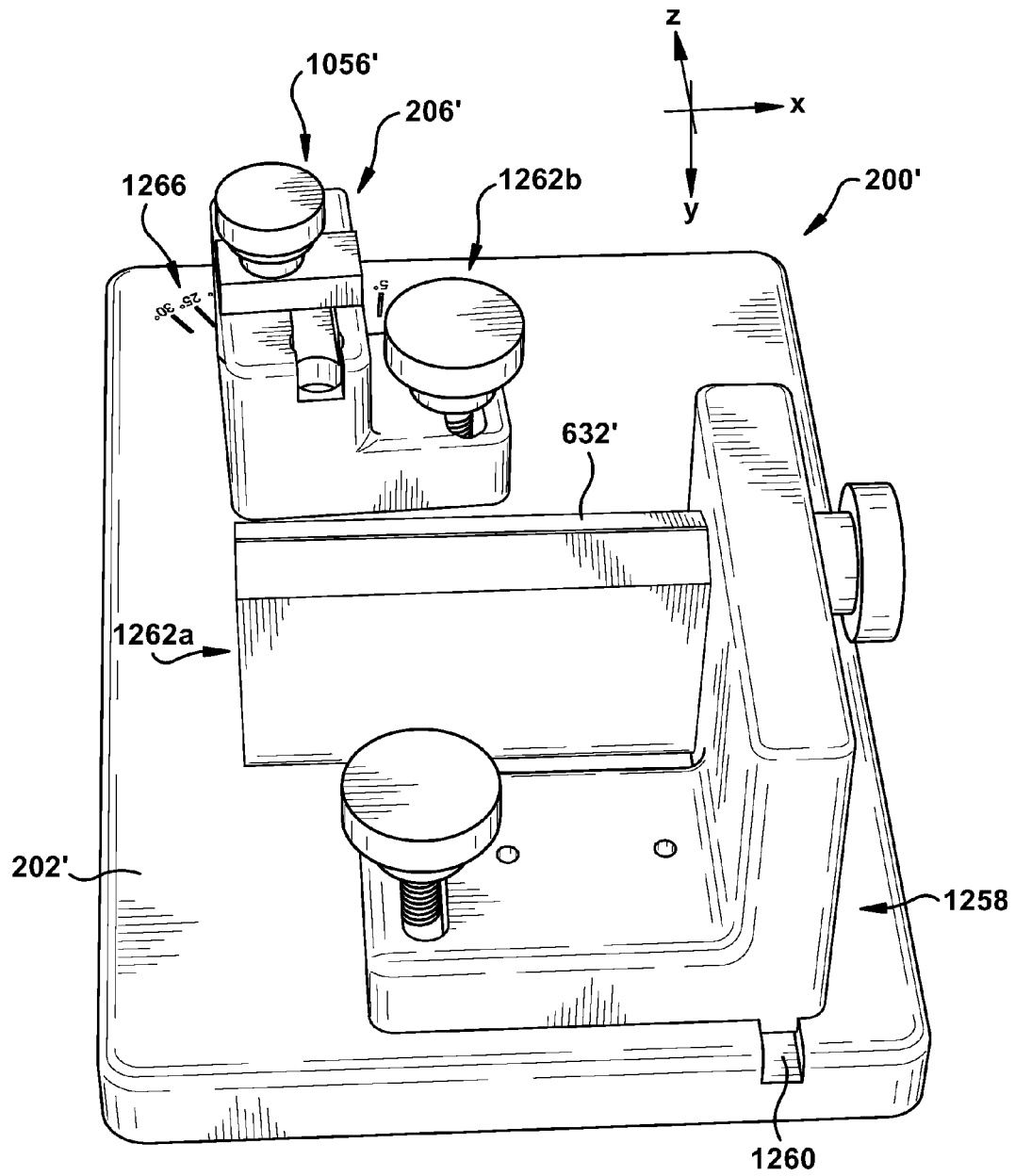
FIG. 14 is a perspective rear view of the embodiment of FIG. 12.
Figure 15:
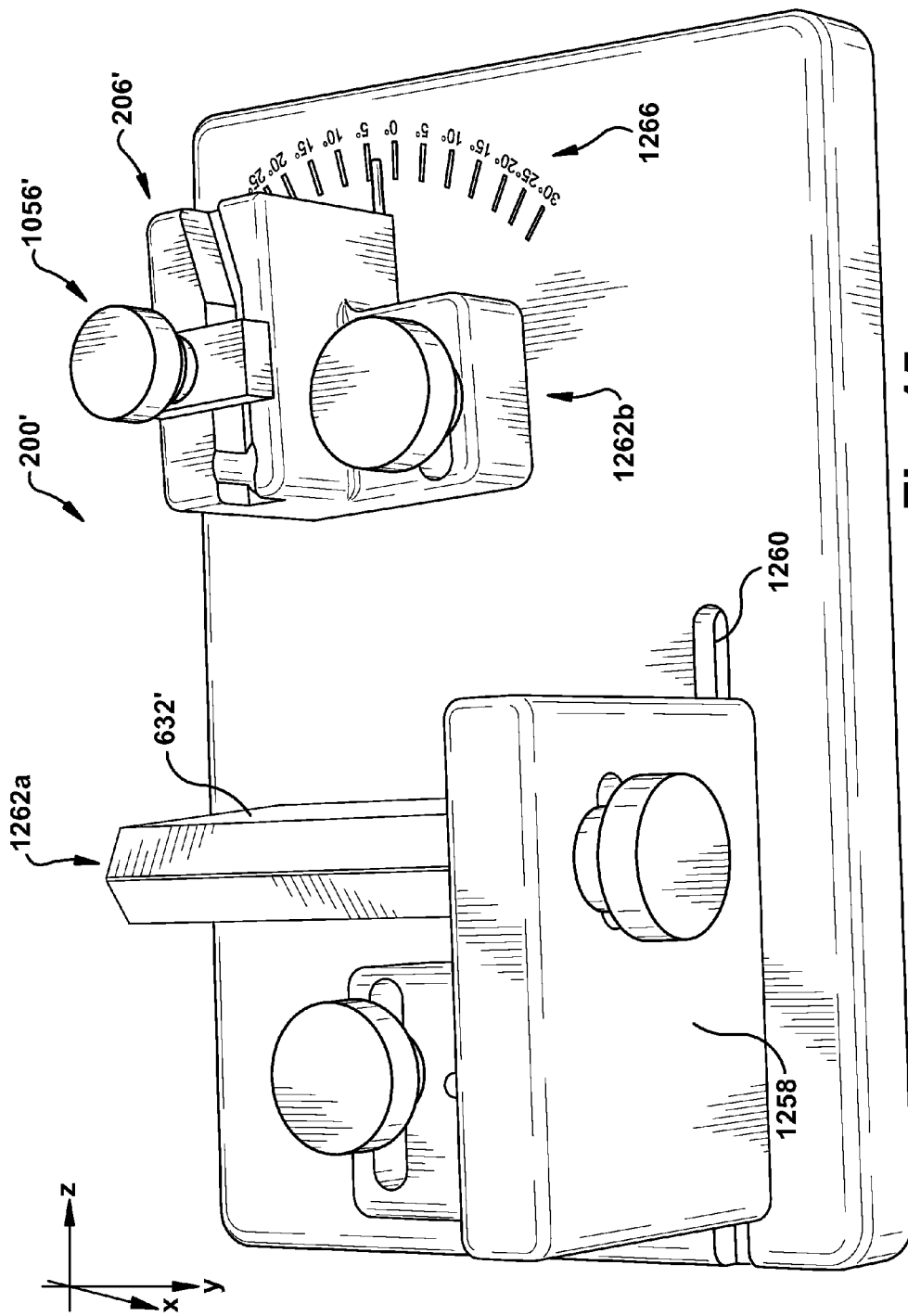
FIG. 15 is a perspective side view of the embodiment of FIG. 12.
Figure 16:
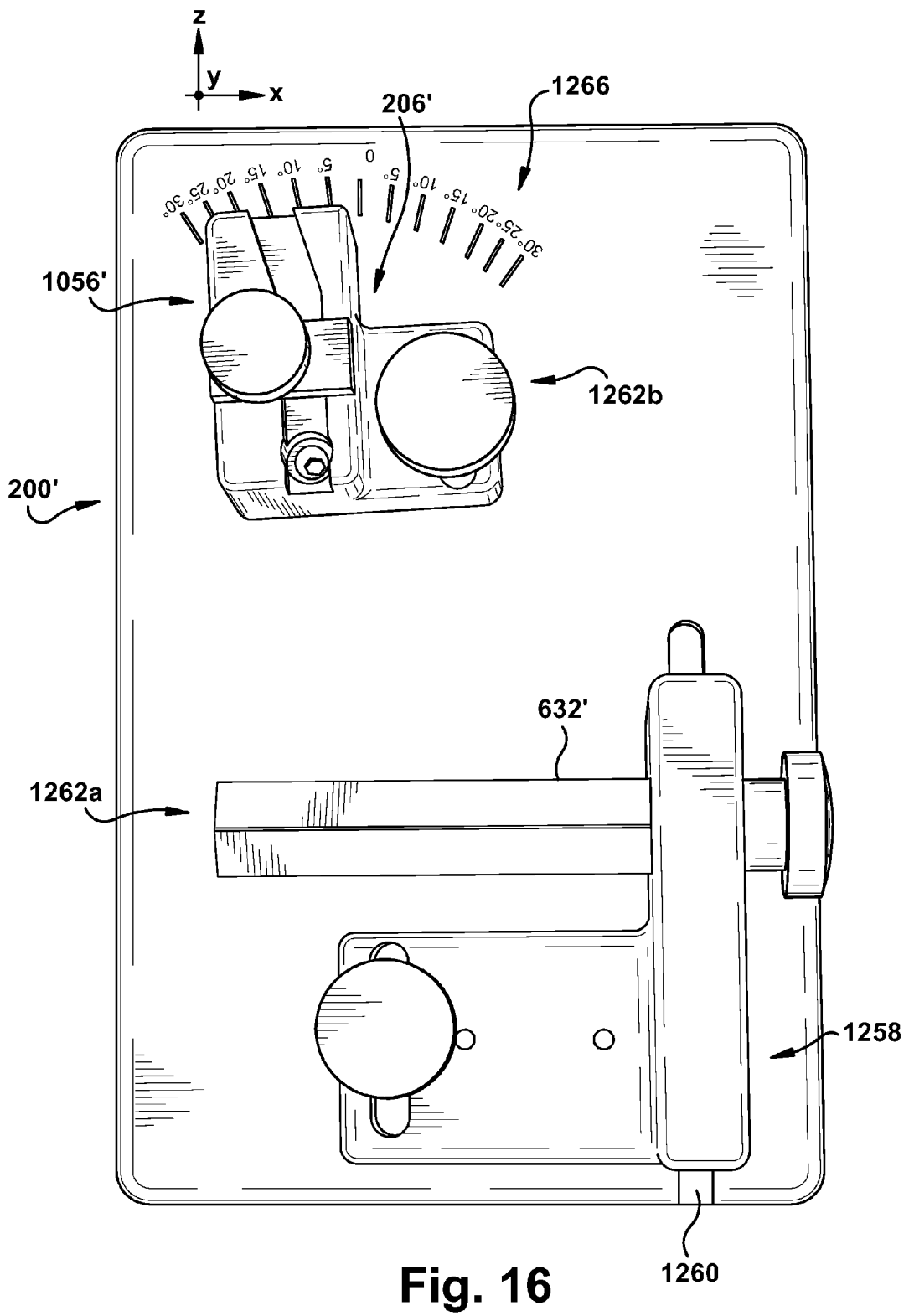
FIG. 16 is a top view of the embodiment of FIG. 12.
Figure 17:
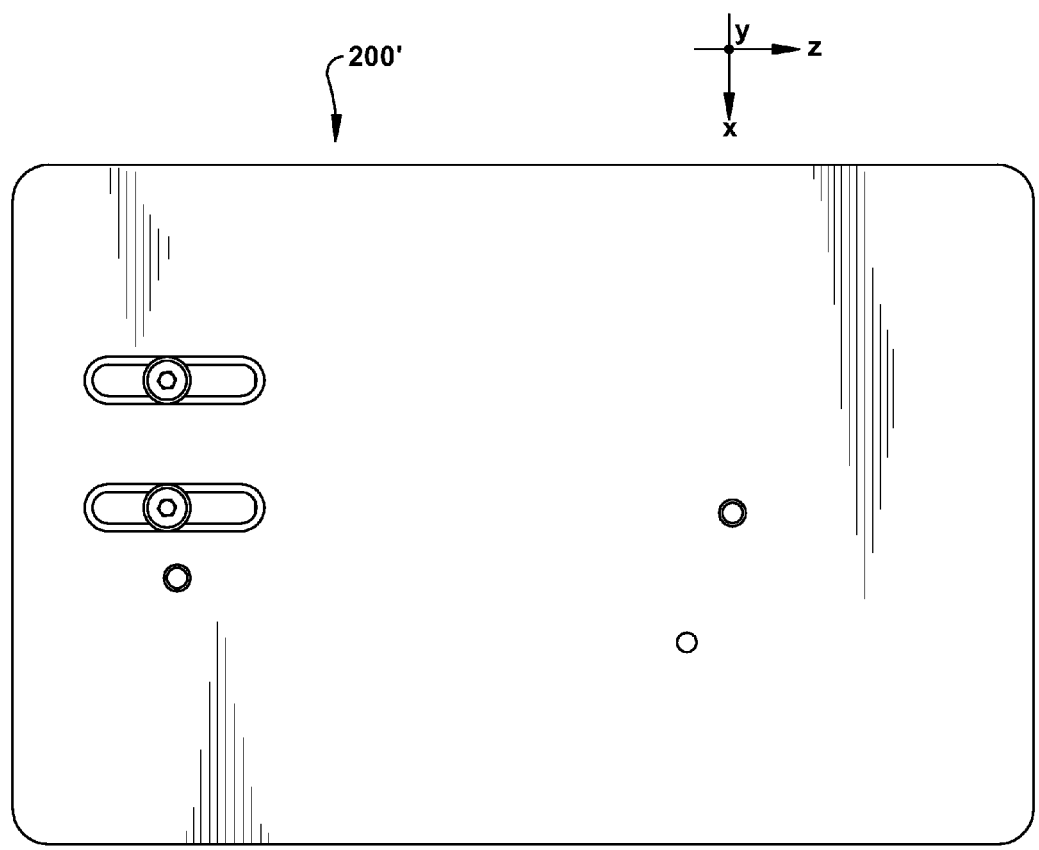
FIG. 17 is a bottom view of the embodiment of FIG. 12.

As shown in FIG. 12, the apparatus 200' of the second embodiment is, like that of the first embodiment, configured to transfer predetermined spatial positioning information to an adjustable tool 1046'. However, the apparatus 200' of the second embodiment does not use a spacing block 630 (patient-specific or otherwise) to support the reference surface 632 as does the apparatus 200 of the first embodiment. Instead, the apparatus 200' of the second embodiment includes an integral reference surface 632'.

A base 202' supports and spaces apart a plurality of adjustable orientation supports, each of which is configured for movement in one or more degrees of freedom (X-axis, Y-axis, Z-axis, pitch, yaw, and roll). To provide the described movement, the base 202' and/or the adjustable orientation supports may include any suitable mechanical arrangement and/or locking mechanism, such as, but not limited to, the various depicted combinations of slots and engageable tightening screws, the operation of which will be apparent to one of ordinary skill in the art and which will not be described herein in detail. At least one adjustable orientation support is configured to impart predetermined spatial positioning information to the reference surface 632' in at least one degree of freedom (X-axis, Y-axis, Z-axis, pitch, yaw, and roll).

Instead of the elongate column 204 of the first embodiment, the second embodiment includes a type of adjustable orientation support which acts as a Z-axis adjuster 1258 by selectively sliding along a Z-axis slot 1260. The Z-axis adjuster 1258 also connects a manipulable reference surface 632' to the base 202'. This connection is made by a pivoting holding block 1262*a* which imparts to the adjustable tool 1046' predetermined spatial positioning information including at least one of pitch, yaw, and roll to the reference surface 632'. In the orientation of FIG. 12, the holding block 1262*a* imparts pitch rotation (about the X axis, in the orientation of the Figures) to the reference surface 632' to help generate the pre-set reference surface. The amount of pitch provided can be specified by adjustment using a pitch scale 1264. The reference surface 632' may include a scale, grid, or other user-perceptible indicator (not shown) which assists the user with dictating, quantifying, and/or observing the relationship between at least a portion of the adjustable tool 1046 (e.g., the trajectory structure 1052 and/or a protruding arm 1159) and the reference surface.

Similarly to the holding block 1262*a* imparting pitch, yaw, and/or roll to the reference surface 632', a pivoting holding block 1262*b* may impart at least one of pitch, yaw, or roll to the reference surface in relation to the tool grasper 206' by allowing pivoting of the tool grasper. Here, the holding block 1262*b* imparts yaw rotation (about the Y axis, in the orientation of the Figures) to the reference surface 632', as guided by a yaw scale 1266. The holding block 1262*b* shown in FIGS. 12-18 is combined with the tool grasper 206'.

Figure 18:
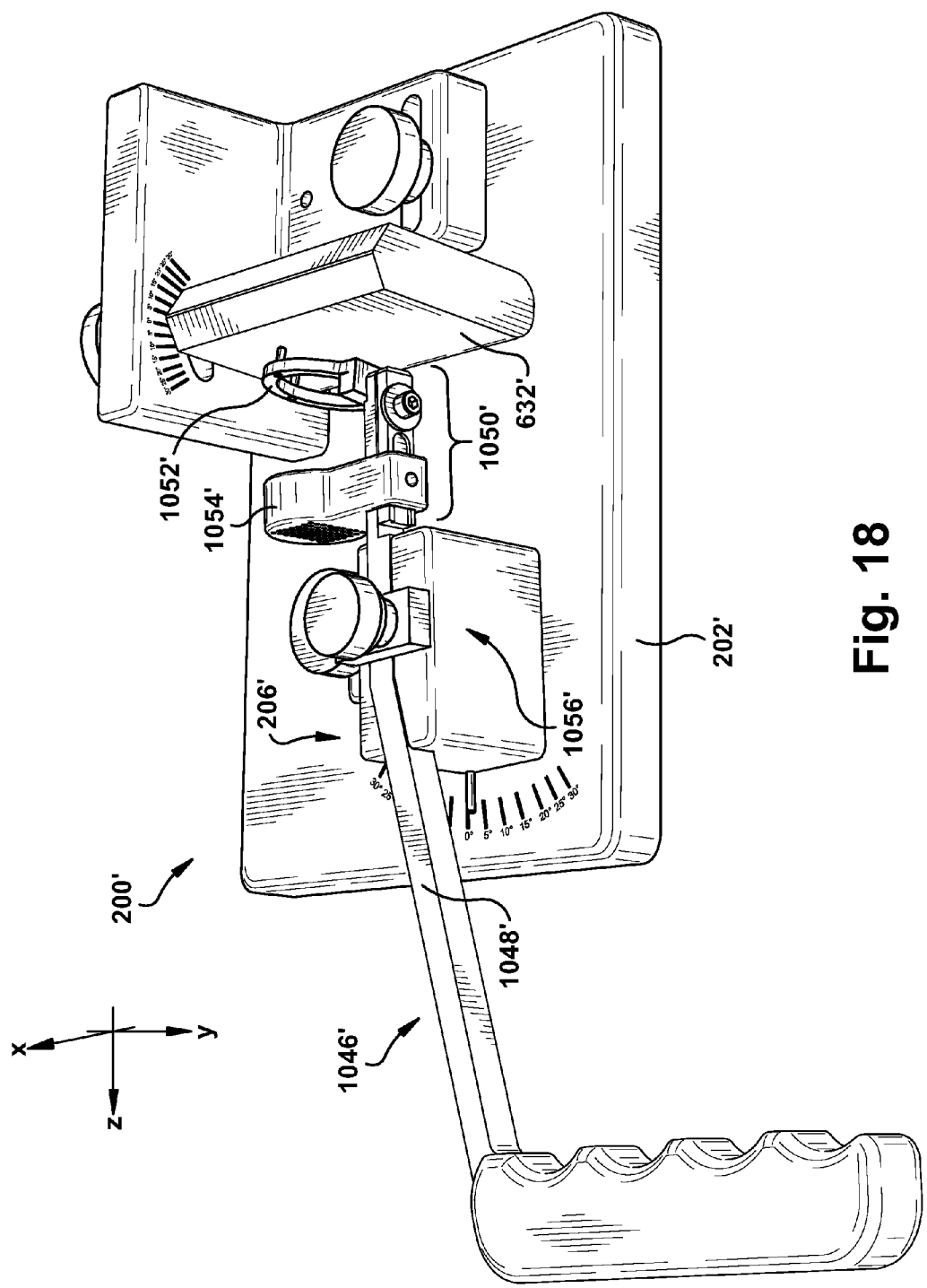
FIG. 18 is a perspective side view of the embodiment of FIG. 12 in a first use arrangement.

The adjustable tool 1046' is depicted in FIG. 18 as being temporarily held stationary relative to the base 202' by the tool grasper 206', with the assistance of the clamping feature 1056'. Presuming that the pre-set reference surface 632' was previously generated, the adjustable tool 1046' will also be held stationary relative by the tool grasper 206' relative to the pre-set reference surface, and at least a functional portion 1050' of the adjustable tool may be manipulated into the predetermined setting position relative to the pre-set reference surface. Because the apparatus 200' is being used to impart predetermined spatial positioning information to the adjustable tool 1046', the predetermined setting position of the adjustable tool will be reflective of a position of the pre-set reference surface 632' in relation to the tool grasper 206'.

The user may pre-set the reference surface 632' using any desired predetermined spatial positioning information. For example, the user may estimate a desired pre-set reference surface 632' position and orientation, which would be done for the Z-axis adjuster 1258 as shown in FIGS. 12-18, since no corresponding scale is provided. As another example, a preoperative planning system (such as the aforementioned system) may output one or more numbers, to which the pitch scale 1264, yaw scale 1266, and any other scales of the apparatus 200' may be set. Any number of scales may be provided to the apparatus 200', for any desired reasons and interacting with the adjustable tool 1046' (or any other adjustable tool) in any desired manner. A patient-specific spacing block may be used with the apparatus 200' of the second embodiment, optionally being placed into contact with (or into any other predetermined relationship with) the holding block 1262a to be held stationary relative to the base 202'; under this arrangement, the reference surface (not shown) of the patient-specific spacing block may supplant the depicted reference surface 632'. Regardless of the way in which the predetermined spatial positioning information is determined and/or embodied in the apparatus 200', one of ordinary skill in the art will recognize that the apparatus 200' of the second embodiment of the present invention assists with the transfer of predetermined spatial positioning information from a pre-set reference surface 632' to an adjustable tool 1046' in a similar manner to that of the apparatus 200 of the first embodiment, described above.

Figure 19:
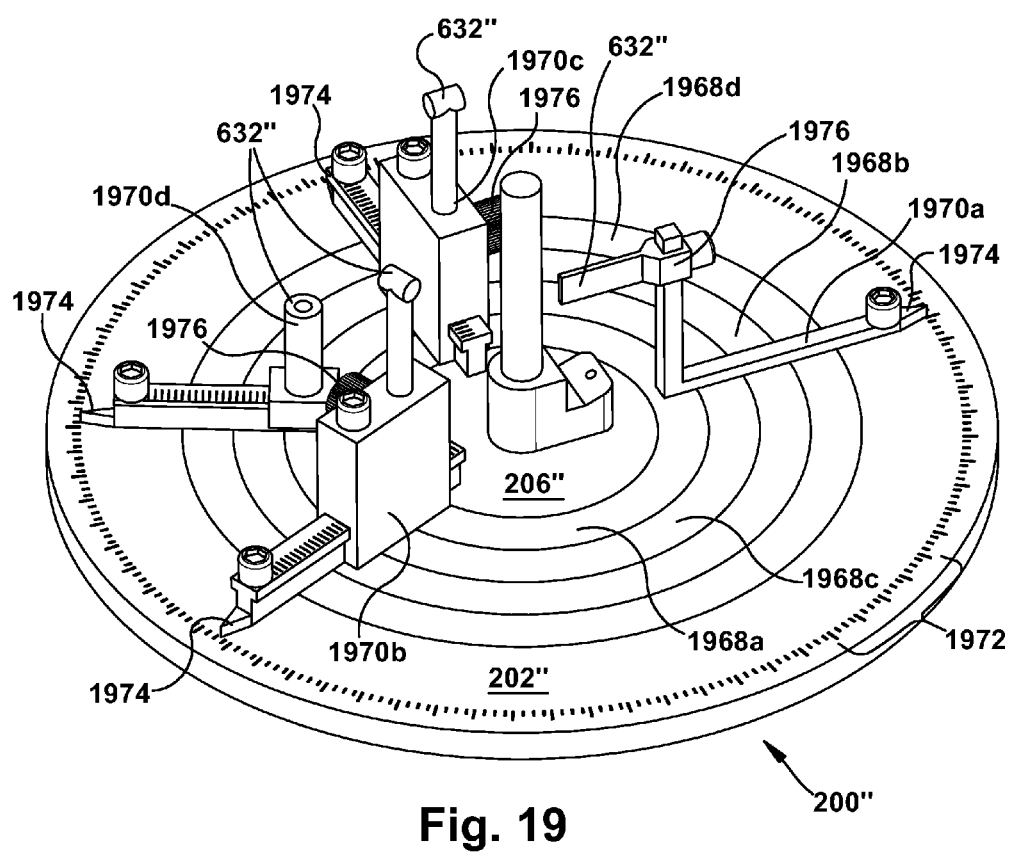
FIG. 19 is a perspective top view of an embodiment of the present invention.
Figure 20:
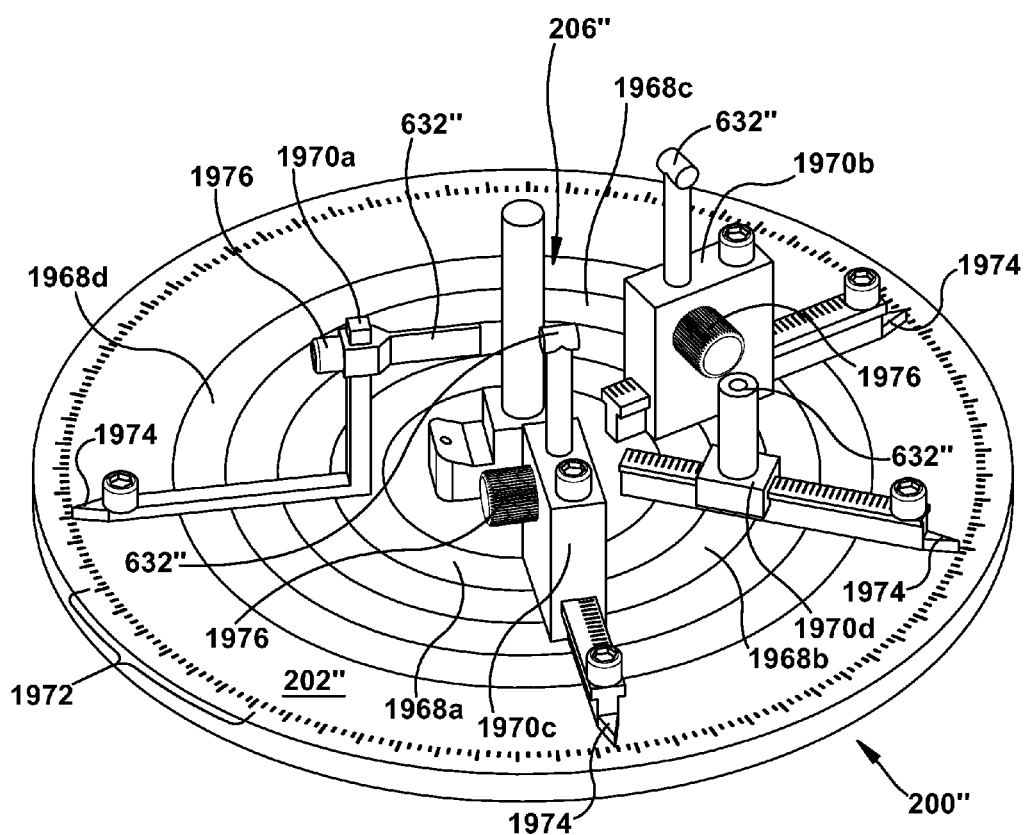
FIG. 20 is a perspective top view of the embodiment of FIG. 19.

FIGS. 19-20 depict an apparatus 200" according to a third embodiment of the present invention. The apparatus 200" of FIGS. 19-20 is similar to the apparatus 200 of FIGS. 1-11B and therefore, structures of FIGS. 19-20 that are the same as, or similar to, those described with reference to FIGS. 1-11B have the same reference numbers with the addition of a double "prime" mark. Description of common elements and operation similar to those in the previously described embodiment will not be repeated with respect to the variation of FIGS. 19-20.

The apparatus 200" of the third embodiment could be used to set an adjustable tool 1046" that differs from the adjustable tool 1046 described with reference to the first and second embodiments. For the below description of the third embodiment, a suitable adjustable tool 1046" is disclosed in co-pending U.S. Provisional Patent Application No. 61/534,152, filed 13 Sep. 2011 and titled "Method and Apparatus for Insertion of an Elongate Pin into a Surface", which is incorporated herein by reference in its entirety. The adjustable tool 1046" used with the third embodiment of the present invention may be useful, for example, in a hip replacement procedure, such as to set the location and/or trajectory of a guide pin within an acetabulum (not shown).

The adjustable tool 1046" for use with the third embodiment comprises a primary leg having a plurality of subordinate legs adjustably (e.g., pivotably) attached thereto. Accordingly, the apparatus 200" of the third embodiment includes a tool grasper 206" configured to hold the primary leg of the adjustable tool 1046" in a relatively fixed, central location with respect to the base 202" of the apparatus. A plurality of setting rings 1968 are located concentrically around the tool grasper 206" and are each configured to rotate about the tool grasper as desired for setting of the adjustable tool 1046".

Each setting ring 1968 has a subordinate leg setting mechanism 1970 carried thereupon, with like suffixes a, b, c, and d indicating linked pairs of setting rings and subordinate leg setting mechanisms in FIGS. 19 and 20. The setting ring 1968 is manipulated to place the corresponding subordinate leg setting mechanism 1970 into a desired rotational position with respect to the tool grasper 206". Optionally, this rotation may be carried out with the aid of an angular scale 1972, located on the periphery of the base 202" or elsewhere on the apparatus 200". When present, the angular scale 1972 can serve as a positioning aid for the rotation of each subordinate leg setting mechanism 1970 when an indicator arrow 1974 shows that the subordinate leg setting mechanism has been rotated to a desired position with respect to the base 202". For example, a preoperative planning software system could indicate particular angular scale 1972 values to which each subordinate leg setting mechanism 1970 can be rotated for desired positioning of the adjustable tool 1046".

Additionally to this rotational/angular setting, each subordinate leg setting mechanism 1970 may include height adjustment means 1976, such as the depicted turnscrews, which allow movement of a portion of the subordinate leg setting mechanism in the Z-direction relative to the base 202". When present, these height adjustment means 1976 may be of any suitable type and may also include a scale (not shown) to provide some indication of the extension or retraction of the height-movable portion(s) of the subordinate leg setting mechanism(s) 1970.

Once the subordinate leg setting mechanism(s) 1970 have been rotationally and vertically adjusted as desired relative to the tool grasper 206", predetermined surfaces on the subordinate leg setting mechanisms 1970 collectively form a reference surface 632", by which the adjustable tool 1046" can be set for the desired trajectory and/or positioning information to be transferred from the apparatus 200" to the native patient tissue.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described system are merely illustrative; one of ordinary skill in the art could readily determine any number of devices, sequences of steps, or other means/options for transferring the predetermined spatial positioning information to the adjustable tool as described. Any of the described structures and components could be integrally formed as a single piece or made up of separate sub-components, with either of these formations involving any suitable stock or bespoke components and/or any suitable material or combinations of materials. It is contemplated that the apparatus 200 may be reusable (optionally sterilizable), and the patient-specific spacing blocks 630 (including bone models 942) may be disposable. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A variety of schemes are described herein for placing the adjustable tool 1046 into the predetermined setting position, and these schemes can be used singly or in any suitable combination for a particular application of the present invention. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for transferring predetermined spatial positioning information to an adjustable tool, the apparatus comprising:
a manipulable reference surface;
means for temporarily holding at least a carrier portion of the adjustable tool stationary relative to the reference surface;
means for imparting predetermined spatial positioning information to the reference surface in a first degree of freedom; and
means for imparting predetermined spatial positioning information to the reference surface in a second degree of freedom; wherein
the predetermined spatial positioning information is imparted to the reference surface in the first and second degrees of freedom to generate a pre-set reference surface, at least the carrier portion of the adjustable tool is then held stationary relative to the pre-set reference surface, and then at least a functional portion of the adjustable tool is manipulated into a predetermined setting position relative to the reference surface, the predetermined setting position being reflective of a position of the pre-set reference surface, and
wherein the means for temporarily holding at least a carrier portion of the adjustable tool stationary relative to the reference surface includes at least one of the means for imparting predetermined spatial positioning information to the reference surface in the first degree of freedom and the means for imparting predetermined spatial positioning information to the reference surface in the second degree of freedom.

2. The apparatus of claim 1, wherein each of the first and second degrees of freedom is selected from the group consisting of: X-axis, Y-axis, Z-axis, pitch, yaw, and roll.

3. The apparatus of claim 1, including means for imparting predetermined spatial positioning information to the reference surface in at least one additional degree of freedom.

4. The apparatus of claim 3, wherein each of the additional degrees of freedom is selected from the group consisting of: X-axis, Y-axis, Z-axis, pitch, yaw, and roll.

5. The apparatus of claim 1, wherein the reference surface is located on a patient-specific bone model.

6. A method of setting an adjustable tool for use in a particular surgical environment, the method comprising the steps of:
providing a manipulable reference surface;
temporarily holding at least a carrier portion of the adjustable tool stationary relative to the reference surface;
imparting predetermined spatial positioning information to the reference surface in a first degree of freedom;
imparting predetermined spatial positioning information to the reference surface in a second degree of freedom;
generating a pre-set reference surface embodying the predetermined spatial positioning information; and
manipulating at least a functional portion of the adjustable tool into a predetermined setting position reflective of the predetermined spatial positioning information embodied in the pre-set reference surface.

7. The method of claim 6, including the steps of:
maintaining the functional portion of the adjustable tool in the predetermined setting position; and
removing the adjustable tool from the stationary relationship with the reference surface with the functional portion of the adjustable tool being maintained in the predetermined setting position.

8. The method of claim 6, wherein each of the first and second degrees of freedom is selected from the group consisting of: X-axis, Y-axis, Z-axis, pitch, yaw, and roll.

9. The method of claim 6, wherein the step of generating a pre-set reference surface embodying the predetermined spatial positioning information includes the step of locating the reference surface on a patient-specific bone model.

10. The method of claim 9, including the steps of:
providing the patient-specific bone model with a first positioning aid;
providing a base attached to the reference surface, the base having a second positioning aid; and
mutually engaging the first and second positioning aids to place the patient-specific bone model into a predetermined relationship with at least a carrier portion of the adjustable tool.

11. The method of claim 6, wherein the step of temporarily holding at least a carrier portion of the adjustable tool stationary relative to the reference surface includes the step of imparting predetermined spatial positioning information to the reference surface relative to the adjustable tool in at least one of the first and second degrees of freedom.

12. An apparatus for transferring predetermined spatial positioning information to an adjustable tool, the apparatus comprising:
a base;
an elongate column extending longitudinally upward from the base;
a tool grasper attached to the elongate column and configured to temporarily hold at least a carrier portion of the adjustable tool stationary in relation to the base; and
a patient-specific spacing block supported by the base, the spacing block including a reference surface embodying predetermined spatial positioning information to be transferred to a functional portion of the adjustable tool; wherein
the spacing block includes a first positioning aid, at least one of the base, the elongate column, and the tool grasper includes a second positioning aid, and the first and second positioning aids are configured for mutual engagement to place the spacing block into a predetermined relationship with the tool grasper and thereby generate a pre-set reference surface.

13. The apparatus of claim 12, wherein the tool grasper is spaced apart from the base by at least a portion of the elongate column.

14. The apparatus of claim 12, wherein the tool grasper includes at least one clamping feature configured to releasably hold at least the carrier portion of the adjustable tool stationary relative to the elongate column.

15. The apparatus of claim 12, wherein a chosen one of the first and second positioning aids includes a male engagement component and the other one of the first and second positioning aids includes a female engagement component, the male and female engagement components cooperatively placing the spacing block into the predetermined relationship with the tool grasper.

16. The apparatus of claim 12, wherein at least one of the first and second positioning aids embodies predetermined spatial positioning information and is operative to transfer the predetermined spatial positioning information to the adjustable tool.

17. The apparatus of claim 12, wherein the predetermined spatial positioning information includes information on the positioning of the reference surface in at least one degree of freedom, the degree of freedom being selected from the group consisting of: X-axis, Y-axis, Z-axis, pitch, yaw, and roll.

18. The apparatus of claim 12, wherein the patient-specific spacing block includes a patient-specific bone model, with the reference surface being a surface of the patient-specific bone model.

19. The apparatus of claim 18, wherein the patient-specific spacing block includes a standardized foundation.

20. The apparatus of claim 18, wherein the patient-specific spacing block includes a patient-specific foundation.

21. The apparatus of claim 12, wherein the functional portion of the adjustable tool is manipulated into a predetermined setting position relative to the reference surface, the predetermined setting position being reflective of the predetermined spatial positioning information.

* * * * *